US009050596B2

(12) United States Patent
Easley et al.

(10) Patent No.: US 9,050,596 B2
(45) Date of Patent: Jun. 9, 2015

(54) PASSIVE COMPONENTS FOR MICRO-FLUIDIC FLOW PROFILE SHAPING AND RELATED METHOD THEREOF

(75) Inventors: Christopher J. Easley, Madison, TN (US); James M. Karlinsey, Audubon, PA (US); James P. Landers, Charlottesville, VA (US); Dan Leslie, Charlottesville, VA (US); Matthew R. Begley, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 14 days.

(21) Appl. No.: 13/474,420

(22) Filed: May 17, 2012

(65) Prior Publication Data
US 2012/0222747 A1  Sep. 6, 2012

Related U.S. Application Data

(62) Division of application No. 12/064,557, filed as application No. PCT/US2006/032717 on Aug. 23, 2006, now Pat. No. 8,220,493.

(60) Provisional application No. 60/710,702, filed on Aug. 23, 2005.

(51) Int. Cl.
*F15C 3/04* (2006.01)
*B01L 3/00* (2006.01)
(Continued)

(52) U.S. Cl.
CPC .... *B01L 3/502738* (2013.01); *Y10T 428/24562* (2015.01); *A61M 2206/22* (2013.01); *B01L 3/502746* (2013.01); *B01L 2200/0621* (2013.01); *B01L 2300/0816* (2013.01); *B01L 2300/0887* (2013.01); *B01L 2400/0487* (2013.01);
(Continued)

(58) Field of Classification Search
CPC .................. B01L 3/502746; B01L 2300/0829; F16K 7/17
USPC ........ 137/825, 829, 833, 510; 251/331, 335.2
See application file for complete search history.

(56) References Cited

U.S. PATENT DOCUMENTS 3,582,037 A   6/1971  Levesque
4,188,977 A   2/1980  Laakaniemi et al.
(Continued)

FOREIGN PATENT DOCUMENTS

AU   2006283177 B2   5/2012
WO   WO-0241994 A2   5/2002
(Continued)

OTHER PUBLICATIONS

"Australian Application Serial No. 2012200887, First Examiner Report mailed May 15, 2013", 3 pgs.
(Continued)

*Primary Examiner* — John K Fristoe, Jr.
*Assistant Examiner* — Minh Le
(74) *Attorney, Agent, or Firm* — Schwegman Lundberg & Woessner, P.A.

(57) ABSTRACT

The present invention relates to microfluidic systems and methods for controlling the flow of fluid using passive components engineered into the microchannels. These passive flow components include fluidic diodes, fluidic capacitors, and fluidic inductors. Various fluidic circuits are provided to control fluid flow including fluid rectifiers, fluid band pass filters, and fluid timers.

14 Claims, 16 Drawing Sheets

(51) Int. Cl.
*F04B 43/04* (2006.01)
*F16K 99/00* (2006.01)

(52) U.S. Cl.
CPC ...... *B01L2400/06* (2013.01); *B01L 2400/0638* (2013.01); *B01L 2400/08* (2013.01); *F04B 43/043* (2013.01); *F16K 99/0001* (2013.01); *F16K 99/0015* (2013.01); *F16K 99/0057* (2013.01); *F16K 2099/008* (2013.01); *F16K 2099/0084* (2013.01)

(56) References Cited

U.S. PATENT DOCUMENTS

| | | | |
|---|---|---|---|
| 5,958,349 | A | 9/1999 | Petersen et al. |
| 6,312,929 | B1 | 11/2001 | McMillan |
| 6,368,871 | B1 | 4/2002 | Christel et al. |
| 6,369,893 | B1 | 4/2002 | Christel et al. |
| 6,374,684 | B1 | 4/2002 | Dority |
| 6,403,037 | B1 | 6/2002 | Chang et al. |
| 6,406,605 | B1 | 6/2002 | Moles |
| 6,431,476 | B1 | 8/2002 | Taylor et al. |
| 6,440,725 | B1 | 8/2002 | Pourahmadi et al. |
| 6,534,645 | B2 | 3/2003 | McMillan |
| 6,565,815 | B1 | 5/2003 | Yuan et al. |
| 6,619,311 | B2 | 9/2003 | O'Connor et al. |
| 6,660,228 | B1 | 12/2003 | Chang et al. |
| 6,664,104 | B2 | 12/2003 | Pourahmadi et al. |
| 6,713,297 | B2 | 3/2004 | McMillan et al. |
| 6,739,531 | B2 | 5/2004 | Taylor |
| 6,783,736 | B1 | 8/2004 | Taylor et al. |
| 6,783,934 | B1 | 8/2004 | McMillan et al. |
| 6,818,185 | B1 | 11/2004 | Petersen et al. |
| 6,819,027 | B2 | 11/2004 | Saraf |
| 6,878,540 | B2 | 4/2005 | Pourahmadi et al. |
| 6,881,541 | B2 | 4/2005 | Petersen et al. |
| 6,887,693 | B2 | 5/2005 | McMillan et al. |
| 6,893,879 | B2 | 5/2005 | Petersen et al. |
| 6,911,327 | B2 | 6/2005 | McMillan et al. |
| 6,940,598 | B2 | 9/2005 | Christel et al. |
| 6,942,971 | B2 | 9/2005 | McMillan et al. |
| 6,979,424 | B2 | 12/2005 | Northrup et al. |
| 6,987,018 | B2 | 1/2006 | Taylor et al. |
| 7,101,509 | B2 | 9/2006 | Chang et al. |
| 7,135,144 | B2 | 11/2006 | Christel et al. |
| 7,188,001 | B2 | 3/2007 | Young et al. |
| 7,226,732 | B2 | 6/2007 | Sakai et al. |
| 7,255,833 | B2 | 8/2007 | Chang et al. |
| 7,294,466 | B2 | 11/2007 | McMillan |
| 7,410,760 | B2 | 8/2008 | Swenson |
| 7,462,323 | B1 | 12/2008 | Chang et al. |
| 7,569,346 | B2 | 8/2009 | Petersen |
| 7,575,721 | B2 | 8/2009 | Chang et al. |
| 7,621,418 | B2 | 11/2009 | Chang |
| 7,687,232 | B2 | 3/2010 | Gyllensten et al. |
| 7,803,549 | B2 | 9/2010 | Swenson |
| 7,914,994 | B2 | 3/2011 | Petersen et al. |
| 8,220,493 | B2 | 7/2012 | Easley et al. |
| 2001/0012612 | A1 | 8/2001 | Petersen et al. |
| 2001/0019114 | A1 | 9/2001 | Arakawa et al. |
| 2002/0019060 | A1 | 2/2002 | Petersen et al. |
| 2002/0025576 | A1 | 2/2002 | Northrup et al. |
| 2002/0029814 | A1 | 3/2002 | Unger et al. |
| 2002/0031768 | A1 | 3/2002 | McMillan et al. |
| 2002/0034745 | A1 | 3/2002 | McMillan et al. |
| 2002/0034746 | A1 | 3/2002 | McMillan et al. |
| 2002/0039783 | A1 | 4/2002 | McMillan et al. |
| 2002/0042125 | A1 | 4/2002 | Petersen et al. |
| 2002/0045246 | A1 | 4/2002 | McMillan et al. |
| 2002/0055167 | A1 | 5/2002 | Pourahmadi et al. |
| 2002/0058282 | A1 | 5/2002 | McMillan et al. |
| 2002/0109844 | A1 | 8/2002 | Christel et al. |
| 2002/0150683 | A1 | 10/2002 | Troian et al. |
| 2002/0155010 | A1 | 10/2002 | Karp et al. |
| 2002/0166585 | A1 | 11/2002 | O'Connor et al. |
| 2002/0168299 | A1 | 11/2002 | Chang et al. |
| 2002/0175079 | A1 | 11/2002 | Christel et al. |
| 2002/0187074 | A1 | 12/2002 | O'Connor et al. |
| 2002/0187547 | A1 | 12/2002 | Taylor et al. |
| 2003/0066915 | A1 | 4/2003 | Taylor |
| 2003/0152492 | A1 | 8/2003 | Chang et al. |
| 2003/0162304 | A1 | 8/2003 | Dority et al. |
| 2003/0164658 | A1 | 9/2003 | Saraf |
| 2003/0221771 | A1 | 12/2003 | Chang et al. |
| 2004/0075073 | A1 | 4/2004 | Claydon et al. |
| 2004/0096819 | A1 | 5/2004 | McMillan et al. |
| 2004/0101859 | A1 | 5/2004 | Moon et al. |
| 2004/0122559 | A1 | 6/2004 | Young et al. |
| 2004/0166031 | A1 | 8/2004 | Taylor et al. |
| 2004/0200909 | A1 | 10/2004 | McMillan et al. |
| 2005/0003374 | A1 | 1/2005 | Swenson |
| 2005/0042137 | A1 | 2/2005 | Petersen et al. |
| 2005/0069898 | A1 | 3/2005 | Moon et al. |
| 2005/0095603 | A1 | 5/2005 | Mokkapati et al. |
| 2005/0194316 | A1 | 9/2005 | Pourahmadi et al. |
| 2005/0244837 | A1 | 11/2005 | McMillan et al. |
| 2005/0255516 | A1 | 11/2005 | McMillan et al. |
| 2006/0014200 | A1 | 1/2006 | McMillan |
| 2006/0019379 | A1 | 1/2006 | Taylor et al. |
| 2006/0027686 | A1 | 2/2006 | Taylor et al. |
| 2006/0068398 | A1 | 3/2006 | McMillan |
| 2006/0068399 | A1 | 3/2006 | McMillan et al. |
| 2006/0169708 | A1 | 8/2006 | Chang |
| 2006/0177844 | A1 | 8/2006 | Ching et al. |
| 2006/0229441 | A1 | 10/2006 | Gall |
| 2006/0275178 | A1 | 12/2006 | Chang et al. |
| 2007/0259362 | A1 | 11/2007 | Sakai et al. |
| 2008/0014114 | A1 | 1/2008 | Van Atta et al. |
| 2008/0038737 | A1 | 2/2008 | Smith et al. |
| 2008/0057572 | A1 | 3/2008 | Petersen et al. |
| 2008/0193946 | A1 | 8/2008 | McMillan |
| 2008/0227090 | A1 | 9/2008 | Sakai et al. |
| 2008/0254532 | A1 | 10/2008 | Chang et al. |
| 2008/0286151 | A1 | 11/2008 | Chang et al. |
| 2008/0286798 | A1 | 11/2008 | Swenson |
| 2009/0047669 | A1 | 2/2009 | Zhang et al. |
| 2009/0062135 | A1 | 3/2009 | Delfour et al. |
| 2009/0217993 | A1 | 9/2009 | Easley et al. |
| 2009/0308886 | A1 | 12/2009 | Chang et al. |
| 2010/0068706 | A1 | 3/2010 | Pourahmadi et al. |
| 2010/0129827 | A1 | 5/2010 | McMillan |
| 2010/0136569 | A1 | 6/2010 | Moon et al. |
| 2010/0233704 | A1 | 9/2010 | Michot et al. |
| 2010/0240049 | A1 | 9/2010 | Svanholm Barrie et al. |
| 2011/0053155 | A1 | 3/2011 | Gall |

FOREIGN PATENT DOCUMENTS

| | | |
|---|---|---|
| WO | WO-2004/061085 A2 | 7/2004 |
| WO | WO-2004061085 A2 | 8/2004 |
| WO | WO-2007024829 A2 | 3/2007 |
| WO | WO-2007024829 A3 | 3/2007 |

OTHER PUBLICATIONS

"Canadian Application Serial No. 2,620,285, Office Action mailed Aug. 27, 2013", 2 pgs.

"European Application Serial No. 06802046.0, Office Action mailed Nov. 7, 2012", 4 pgs.

"U.S. Appl. No. 12/064,557 , Response filed Feb. 23, 2012 to Non Final Office Action mailed Aug. 30, 2011", 12 pgs.

"U.S. Appl. No. 12/064,557, Non Final Office Action mailed Aug. 30, 2011", 12 pgs.

"U.S. Appl. No. 12/064,557, Notice of Allowance mailed Mar. 22, 2012", 8 pgs.

"U.S. Appl. No. 12/064,557, Response file Jul. 14, 2011 to Restriction Requirement mailed Jun. 15, 2011", 7 pgs.

"U.S. Appl. No. 12/064,557, Restriction Requirement mailed Jun. 15, 2011", 5 pgs.

"Australian Application Serial No. 2006283177, First Examiner Report mailed Mar. 15, 2010", 2 pgs.

(56) References Cited

OTHER PUBLICATIONS

"Australian Application Serial No. 2006283177, Office Action Response Filed Apr. 15, 2011", 6 pgs.
"Australian Application Serial No. 2006283177, Response filed Oct. 14, 2011 to Office Action mailed May 13, 2011", 5 pgs.
"Australian Application Serial No. 2006283177, Subsequent Examiner Report mailed May 13, 2011", 2 pgs.
"European Application Serial No. 06802046.0, Extended European Search Report mailed Aug. 13, 2010", 8 Pgs.
"European Application Serial No. 06802046.0, Office Action mailed Apr. 15, 2011", 4 pgs.
"European Application Serial No. 06802046.0, Response filed Mar. 28, 2011 to EP Search Report mailed Aug. 13, 2010", 9 pgs.
"European Application Serial No. 06802046.0, Response filed Aug. 9, 2011 to Non Final Office Action dated Apr. 15, 2011", 5 pgs.
"International Application Serial No. PCT/US2006/032717, International Preliminary Examination Report mailed Mar. 10, 2009", 7 pgs.
"International Application Serial No. PCT/US2006/032717, Written Opinion mailed Jul. 31, 2008", 6 pgs.
Hasselbrink, Ernest F, et al., "High-Pressure Microfluidic Control in Lab-on-a-Chip Devices Using Mobile Polymer Monoliths", Anal. Chem. 2002, 74, 4913-4918 Sandia National Laboratories, P.O. Box 969, Livermore, California 94551, (2002), 4913-4918.
"Canadian Application Serial No. 2,620,285, Office Action mailed Aug. 18, 2014", 2 pgs.
"Canadian Application Serial No. 2,620,285, Response filed Feb. 14, 2014 to Office Action mailed Aug. 27, 2013", 10 pgs.
"European Application Serial No. 06802046.0, Office Action mailed Nov. 20, 2014", 4 pgs.

PASSIVE COMPONENTS FOR MICRO-FLUIDIC FLOW PROFILE SHAPING AND RELATED METHOD THEREOF

This application is a divisional of and claims the benefit of priority under 35 U.S.C. §120 to U.S. patent application Ser. No. 12/064,557, filed Sep. 18, 2008, which is a U.S. National Stage Filing under 35 U.S.C. §371 of PCT Patent Application Serial No. PCT/US2006/032717, filed Aug. 23, 2006, and published as WO 2007/024829, which claims the benefit of priority under 35 U.S.C. §119(e) to U.S. Provisional Patent Application Ser. No. 60/710,702, filed Aug. 23, 2005, the benefit of priority of each of which is claimed hereby, and each of which is incorporated by reference herein in its entirety.

FIELD OF THE INVENTION

The present invention relates to microfluidic systems and methods for controlling the flow of fluid using passive components engineered into the microchannels.

BACKGROUND OF THE INVENTION

Micro-total analysis systems (μ-TAS or Microfluidic chips) may be used for biological or chemical assays. For example, μ-TAS may be used to perform biological assays using external control lines that control the opening and closing of on-chip fluidic valves which control the flow of fluids in biological assays. The valves are opened and closed using macroscopic pressure sources that are located off-chip, and which are connected through control lines to the chip.

Micro-fluidic valves have been successfully developed using multilayer soft lithography or layering with patterned rigid and elastomeric materials. These methods hold discernible advantages over micro electromechanical (MEMS) valves such as ease of fabrication, simplicity of design, and low actuation force requirements. Individual valves of this kind can be compared to an electronic switch, where an outside stimulus is required for control. This technology has been combined and utilized for the fabrication and operation of micro-fluidic on/off valves, switching valves, and pumps.

A limitation of these types of approaches is that, because each individual valve is analogous to an electronic switch, each valve requires a separate pressure (positive or negative) control line. This type of component can be classified as an active micro-fluidic component. Multiple valves, pumps, etc., are desirable for most applications; in some cases, a large number of these active components are needed. In these cases, the instrumentation needed for control of these miniaturized devices becomes overwhelming with respect to complexity, cost, and space requirements. Especially in complex assays, a large number of macroscopic control lines are cumbersome and undesirable.

It is desirable to provide passive micro-fluidic components that allow defined flow control at the small volume scale (microliter, nanoliter, picoliter, or smaller) and are easy to fabricate. Fluidic components analogous to electrical resistors, diodes, inductors, and capacitors could provide this control without the necessity for control lines. Micro-fluidic valves could be used only when absolutely necessary, and the controlling instrumentation could be miniaturized to a scale comparable or more fitting to the microchip scale and platform.

Passive components with diode-like behavior have been developed previously (Holtz at al., *Anal. Chem*, 1998, 70 (4):780-791; Adams et al., *J. Micromech. Microeng.* 2005, 15:1517-1521), but these components require multilayer fluid flow and more complex patterning than is desired. Nonetheless, with these types of components, the development of 'smart' devices becomes a possibility, in which the fluid control features are built entirely into the devices and not the instrumentation.

Therefore, there remains a need for passively controlling fluid flow in a μ-TAS, without requiring complex control instrumentation or control lines, that can be manufactured inexpensively and easily.

SUMMARY OF THE INVENTION

It is an object of the present invention to provide passive methods and apparatus for precise fluidic control of small volumes.

It is another object of the present invention to provide a fluidic diode that allows for flow rectification via fluid flow only in one direction.

It is yet another object of the present invention to provide a fluidic capacitor that provides means for energy storage in the form of fluid volume.

It is yet another object of the present invention to provide a fluidic inductor that provides means for energy storage in the form of heat.

It is yet another object of the present invention to provide a fluidic circuit having various combinations of fluid fluidic diode, fluidic capacitor, and/or fluidic inductor to passively controlling fluid flow.

The major advancement of the present invention is the ability to achieve precise fluid control of small volumes without the necessity for instrumentation and hardware to realize on-chip actuation. The passive micro-fluidic diodes, capacitors, inductors, and combined circuits of each provide this capability. For example, FIG. 1 illustrates a micro-fluidic channel architecture in which eight input solutions are required to be added in any combination to reaction chamber 9. In any configuration, the device requires eight pressure input lines (1-8), one for each respective solution. Without the use of valves or passive components (FIG. 1A), there is nothing to prevent backflow of solutions into reservoirs 1-8. If active valves are utilized for control, with a prior art design [2] (FIG. 1B), eight separate vacuum or pressure lines and eight separate digital output lines are required for control and to prevent backflow. However, with the use of a passive micro-fluidic diode (FIG. 1C), the nature of the components prevent backflow, providing the desired functionality without the necessity of any instrumentation other than pressure sources for the input solutions. Furthermore, eight digital lines is a limitation on most computer-based data acquisition and control cards. In this example, additional functionality on the valved chip would require multiple cards, introducing additional hardware requirements and expense.

To achieve the above advantages, layered micro-fluidic devices are provided which include one or more rigid layer. The rigid substrate can be any material, including, but not limited to, silicon, glass, ceramics, polymers, metals, and/or quartz, provided that the material is chemically compatible with the solution of flowing through the various channels and components in the rigid substrate. Preferably the rigid substrate has a thickness of about 0.5-10.0 mm, preferably about 1-5 mm. The elastomeric layer can be any deformable material, including, but not limited to, polymers such as polydimethylsiloxane (PDMS), polymethylmethacrylate (PMMA) polyisoprene, polybutadiene, polychloroprene, polyisobutylene, poly(styrene-butadiene-styrene), polyurethanes, silicone polymers, poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene)copolymer (Viton), elastomeric compositions of polyvinylchloride (PVC), polysulfone, polycarbonate, polytertrafluoroethylene (Teflon), or blends thereof; or semi-rigid substrates. Preferably, the elastomeric layer has a thickness of about 5 µm-10 mm, preferably about 5 µm-100 µm, and most preferably about 5 µm-10 µm. The devices may also include a temperature-controlled plate layer. In a preferred embodiment, the elastomeric layer is sandwiched between two rigid layers, where fluid flow is in one of the rigid layer, while the other rigid layer provides recesses for the deflection of the elastomeric layer due to fluid forces. In this configuration, the fluid is constricted to flow in one of the rigid layer, while the elastomeric layer provides the valving or storing function. The devices may also contain entirely of deformable materials, including, but not limited to, polymers such as polydimethylsiloxane (PDMS), polymethylmethacrylate (PMMA) polyisoprene, polybutadiene, polychloroprene, polyisobutylene, poly(styrene-butadiene-styrene), polyurethanes, silicone polymers, poly(bis(fluoroalkoxy)phosphazene) (PNF, Eypel-F), poly (carborane-siloxanes) (Dexsil), polyacrylonitrile-butadiene) (nitrile rubber), to poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene)copolymer (Viton), elastomeric compositions of polyvinylchloride (PVC), polysulfone, polycarbonate, polytertrafluoroethylene (Teflon), or blends thereof. In this case, these elastomeric layers have a thickness of 5 µm-2 cm. Because the flow can be constricted to one layer, only one patterned layer requires solution compatibility.

The devices of the present invention include passive flow control components that provide precise fluidic control without the necessity for outside control lines, thereby greatly reducing instrumentation requirements. The passive components are presented as analogs to circuit components in the electronic arts, and thus can be combined in a similar manner. The passive flow components of the present invention include fluidic diodes, fluidic capacitors, and fluidic inductors.

The fluidic diode provides a directional bias to fluid flow, which can be compared to a diode in the electronic art. The device contains a first layer, preferably a rigid layer, having a microfluidic channel for fluid or gas flow (fluid path); a second layer having a recess patterned therein, which is preferably fabricated in rigid or elastomeric material; and a third layer of elastomeric material sandwiched between the first and second layers such that the chamber of the second layer is directly above the channel of the first layer and separated therefrom by the elastomeric third layer. Fluid flow in the device can be restricted, but not limited to, flow in the first layer. The fluidic diode is designed such that there is a discontinuity in a microfluidic channel in the first layer, which is located directly under the chamber of the second layer. In a preferred embodiment, immediately on the upstream side of the discontinuity, the microchannel is significantly wider than the channel immediately down stream of the discontinuity, preferably about 2-1000 times wider, most preferably about 10-100 times wider. When the fluid pressure upstream of the discontinuity provides sufficient force to deflect the elastomeric layer upward, away from the discontinuity, flow along the channel is effected. On the other hand, fluid flow in the reverse direction is inhibited because the more narrow down stream channel does not generate sufficient force to deflect the more restricted elastomeric layer. As such, flow in only one direction is effected. In another embodiment, the directional bias can be restrictive to negative pressures (vacuum), while allowing flow of positive pressures in either direction. In this embodiment, the geometry on either side of the discontinuity can be equal. Importantly, negative pressure will prevent flow through the diode in either direction, using any geometrical configuration.

The fluidic capacitor provides a means for energy storage in the form of fluid volume, and is analogous to a capacitor in the electronic art. The device contains a first layer containing a microfluidic channel for fluid or gas flow (fluid path) thereon, which is preferably fabricated on a rigid material; a second layer having a recess thereon, preferably fabricated on a rigid material; and a third layer of elastomeric material sandwiched between the first and second layer such that the chamber of the second layer is directly above the channel of the first layer and separated therefrom by the elastomeric third layer. In certain embodiments, the third layer can contain multiple sublayers. This device allows for volume storage in the mechanically deflected elastomeric layer; and its action is modeled by comparison to the capacitor in the electronic arts, with similar equations and characteristics. When the pressure in the channel is sufficient to deflect the elastomeric layer into the chamber of the second layer, the volume of the channel in the first layer increased to store fluid; and when the pressure drops the elastomeric layer contracts to its resting position to allow the stored fluid to flow out of the fluidic capacitor. The capacitor functions equally in either direction. When a negative pressure is present in the channel, the elastomeric layer (third layer) deflects into the chamber of the first layer, thereby storing a negative volume.

The fluidic inductor provides a means for energy storage in the than of heat. The device consists of a first layer containing a channel or chamber for either fluid or gas flow, which can be fabricated in rigid or elastomeric material; a second layer of elastomeric material overlays the channel or chamber of the first layer; and a third layer containing of a temperature-controlled plate, which should be made of a rigid material suitable for localization and transfer of heat into any of the other three layers. Fluid flow in the device can be restricted, but not limited to, flow in the first layer. This component provides a means for energy storage in the form of heat. The heat is stored in the localized patterned component by the temperature-controlled plate (third layer), and any changes in flow will be modulated by the changes in density of the fluid or gas. The action of this component is analogous to the inductor in the electronic art, with similar equations and characteristics Furthermore, these devices are not limited to electronic arts analogies, for they could be based on novel circuits that exploit behaviors unavailable with electrical flow. For example, chemical differences and/or interactions between the flowing solutions provide a realm of study not available with electrical flow.

The present invention also provides a passive component for measurement of fluid pressure. The device consists of a single patterned layer in a rigid or elastomeric material that can be combined with any number of other layers. This component consists of a flow channel analogous to a fluidic resistor and provides a means to measure the pressure at any point in a fluidic circuit. This fluidic resistance should be kept at a larger value (at least 10 times larger, preferably 100-1000 times larger) than that of the channel being measured in order to minimize interference and should be placed in parallel to the fluidic circuit of interest. The pressure profile can thus be visualized through any optical means, monitored by electrical means, or interrogated through any other analytical means known in the art. The action of this component is similar to a voltmeter in the electronic arts, which typically places a high resistor in parallel to measure voltage. This component is referred to as a fluidic pressure meter.

Several micro-fluidic devices are presented that contain combinations of the aforementioned components for passive manipulation or measurement of fluid or gas flow. The devices consist of several combinations of patterned layers, elastomeric layers, or temperature controlled plate layers. Circuit combinations with these passive components are based on the analogous circuits in the electronic arts. Fluid flow in the devices can be restricted, but not limited to, flow in the first layer; and devices are not limited in the number of total layers used. These devices include, but are not limited to, the following: fluidic half-wave rectifiers, full-wave rectifiers, or bridge rectifiers; fluidic low-pass filters (or integrators), high-pass filters (or differentiators), band-pass filters, or other flow transformers; fluidic pressure multipliers, fluidic timers, fluidic diode logic gates. In combination with active components (e.g., valves, latches) present in the prior art, these passive components should provide enhanced flexibility for fluid control, while reducing instrumentation requirements.

DETAILED DESCRIPTION OF THE PREFERRED EMBODIMENTS

Figure 1:
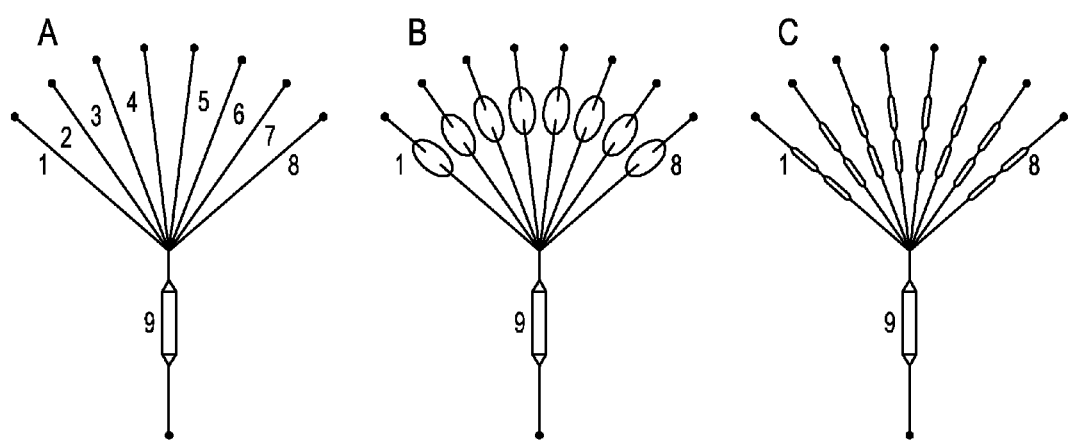
FIG. 1 is a drawing showing an example of a microdevice configuration consisting of eight different input channels (1-8) leading into a single reaction chamber (9). (A) With the inability to control fluid flow (e.g. no valves or directional components) solution from any input channel can enter any other channel. (B) With valves on channels 1-8 (shown as ovals around discontinuous channels) it is possible to control fluid flow into chamber 9, but active control lines are required for valve actuation. (C) With the proposed passive diodes, it is possible to control the flow from channels 1-8 into chamber 9 with no need for actuation lines.

The present invention is generally directed to microfluidic systems and methods for controlling the flow of fluid using passive components engineered into the microchannels. The term "microfluidic" as used herein refers to an apparatus for analysis of small volumes of sample, and containing microscale components for fluid processing, such as channels, pumps, micro-reaction chambers, electrophoresis modules, microchannels, fluid reservoirs, detectors, valves, or mixers. These microfluidic apparatuses are also referred to as micro-total analysis systems (µTAS). "Micro" as used herein refers to small components and is not restricted to micron size scale or microliter volume scale, but also include smaller components in the nanometer size scale or nanoliter to picoliter volume ranges. The passive components used to control fluid flow of the present invention are fluidic diodes, fluidic capacitors, and fluidic inductors.

Microfluidic devices typically include micromachined fluid networks. Fluid samples and reagents are brought into the device through entry ports and transported through channels to a reaction chamber, such as a thermally controlled reactor where mixing and reactions (e.g., synthesis, labeling, energy-producing reactions, assays, separations, or biochemical reactions) occur. The biochemical products may then be moved, for example, to an analysis module, where data is collected by a detector and transmitted to a recording instrument. The fluidic and electronic components are preferably designed to be fully compatible in function and construction with the reactions and reagents.

There are many formats, materials, and size scales for constructing microfluidic devices. Common microfluidic devices are disclosed in U.S. Pat. No. 6,692,700 to Handique et al.; U.S. Pat. No. 6,919,046 to O'Connor et al.; U.S. Pat. No. 6,551,841 to Wilding et al.; U.S. Pat. No. 6,630,353 to Parce et al.; U.S. Pat. No. 6,620,625 to Wolk et al.; and U.S. Pat. No. 6,517,234 to Kopf-Sill et al.; the disclosures of which are incorporated herein by reference. Typically, a microfluidic device is made up of two or more substrates or layers that are bonded together. Microscale components for processing fluids are disposed on a surface of one or more of the substrates. These microscale components include, but are not limited to, reaction chambers, electrophoresis modules, microchannels, fluid reservoirs, detectors, valves, or mixers. When the substrates are bonded together, the microscale components are enclosed and sandwiched between the substrates.

For the present invention, a three layer construction is preferred, where two substrates sandwich a layer of elastomeric material. The fluidic paths and microscale components are patterned on the surface of one of the substrates, while the other substrate contains recesses for the deflection of the elastomeric material where desired. Although these embodiments present a three-layer device, it may be desirable to use multiple layer patterning in the third, elastomeric layer to achieve locally differing elastic behaviors.

In many embodiments, inlet and outlet ports are engineered into the device for introduction and removal of fluid from the system. The microscale components can be linked together to form a fluid network for chemical and/or biological analysis. Those skilled in the art will recognize that rigid substrates composed of silicon, glass, ceramics, polymers, metals, and/or quartz are all acceptable in the context of the present invention. Those skilled in the art will also recognize that semi-rigid or elastomeric substrates, composed of polydimethylsiloxane (PDMS), polymethylmethacrylate (PMMA)

polyisoprene, polybutadiene, polychloroprene, polyisobutylene, poly(styrene-butadiene-styrene), the polyurethanes, and silicone polymers, poly(bis(fluoroalkoxy)phosphazene) (PNF, Eypel-F), poly(carborane-siloxanes) (Dexsil), poly (acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene)copolymer (Viton), elastomeric compositions of polyvinylchloride (PVC), polysulfone, polycarbonate, polytetrafluoroethylene (Teflon), and blends thereof, are all acceptable in the context of the present invention. Further, the design and construction of the microfluidic network vary depending on the analysis being performed and are within the ability of those skilled in the art. In addition to the substrates or layers of the prior art used in the construction of microfluidic devices, the present invention also incorporates elastomeric materials to effect passive components for controlling fluid flow, which include fluidic diodes, fluidic capacitors, and fluidic inductors.

Fluidic Diodes

Figure 2:
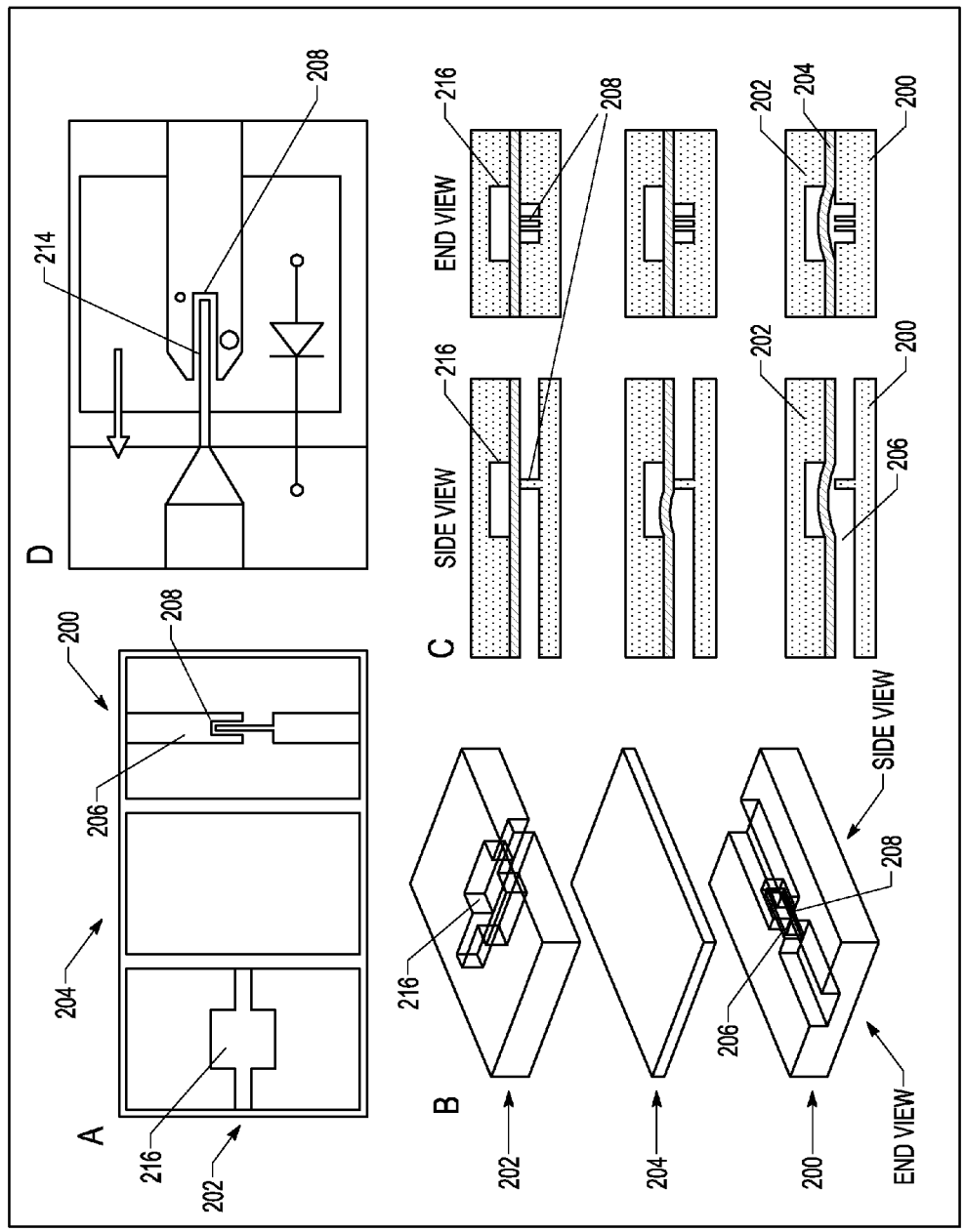
FIG. 2 are drawing showing various views of a preferred embodiment of the fluidic diode component. (A) Overhead 2-D view of each layer. (B) 3-D view of the stacked device, showing the alignment of the discontinuity in layer 200 with the recess in layer 202, separated by the elastomeric layer 204. (C) Side-on and end-on views of the assembled device. In the top figure, the device is unaffected and the diode is in its resting state. In the middle figure, flow is directed from one-end of the device and cannot activate the diode because the component resists the flow pressure. In the bottom figure, flow is directed in the opposite direction and an equal pressure is enough to activate the passive diode. The resulting deflection of the elastomer membrane into the layer above allows fluid to flow through the diode. (D) A microscope image of a dye filled device showing biased flow from right to left across an arbitrary diode geometry. The circuit analog is provided in the inset.
Figure 3:
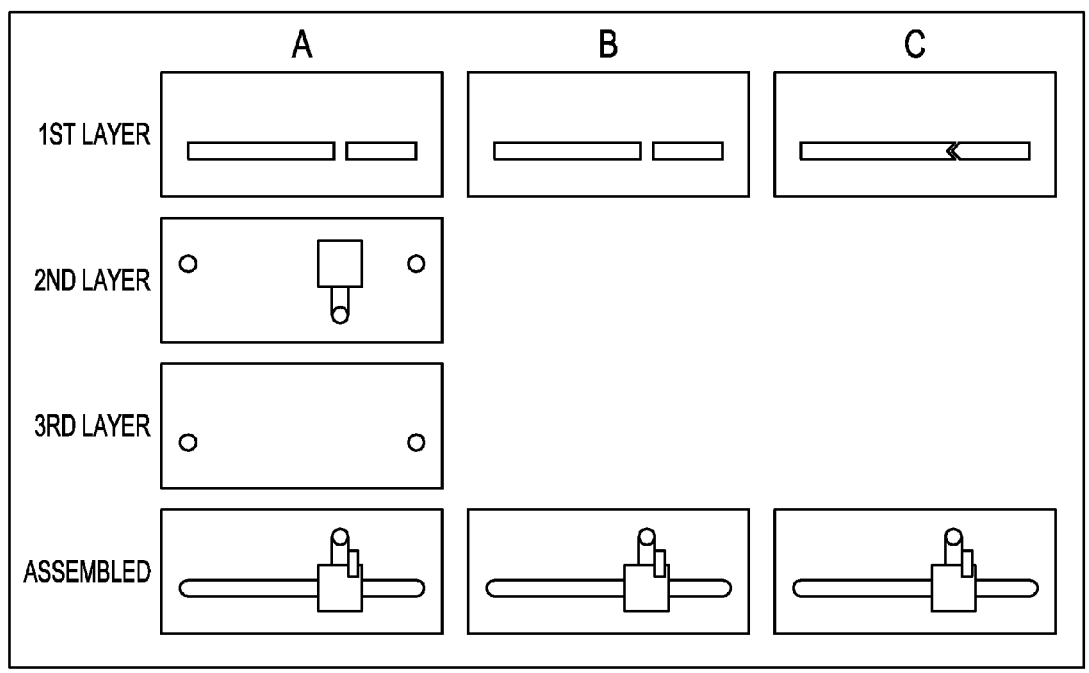
FIG. 3 is a drawing showing the top view of each of the layers of a fluidic diode. (A) Two-dimensional layout of each layer in the fluidic diode, along with the assembled (stacked) device. Note that the $2^{nd}$ layer is a mirror image of that in the assembled device, owing to the manner in which the surfaces are aligned and bonded. Access holes for fluid reservoirs are included in the $2^{nd}$ and $3^{rd}$ layers to bring solution to the fluid channels in the $1^{st}$ layer. An access hole that acts as a pressure ground for the diode component is included in the $2^{nd}$ layer. (B) An example of a fluidic diode where the patterned $1^{st}$ layer consists of the same geometry on either side of the discontinuity. (C) An example of a fluidic diode where the patterned $1^{st}$ layer consists of a different geometry on either side of the discontinuity. Note that the geometry will define whether there is a directional bias to positive pressures, but the geometry is arbitrary for negative pressures. Note that the example geometries shown in FIG. 3 are chosen merely for demonstration purposes.

An embodiment of the fluidic diode is shown in FIGS. 2-3 which comprises three layers 200, 202 and 204. The first layer 200 and the second layer 202 are preferably rigid substrates having microfluidic components thereon. Although rigid substrates are preferred, in certain embodiments theses layers 200 and 202 may be composed of semi-rigid or elastomeric material. The third layer 204 is an elastomeric material that is deflectable by fluid forces flowing through the fluidic diode. This component is characterized by a discontinuous fluidic path 206 in the first layer 200, such that if the third layer 204 was sealed against the patterned side of the first layer no fluid could flow across the discontinuous path. The patterned side of the second layer 202 is then sealed against the opposite side of the third layer 204, forming a three-layer device in the simplest embodiment with the third layer 204 sandwiched between the patterned sides of the first and second layer 200 and 202.

The first layer 200 is patterned with a fluidic path 206 having a discontinuity 208 therein. In a preferred embodiment, the fluidic path 206 is patterned such that, immediately upstream of the discontinuity 208, the fluid path 206 is significantly wider than the fluid path 206 immediately down stream of the discontinuity 208. As illustrated in FIG. 2, the upstream fluid path contains a notch 214 where the smaller, down stream fluid path fits therein. Other configurations for the discontinuity 208 may also be effected as illustrated in FIG. 3. It is desirable, but not necessary, that the fluid path is designed such that at a given pressure, the fluid force at the upstream to fluid path is sufficient to deflect the elastomeric (third) layer 204, while the same pressure at the downstream fluid path is not sufficient to deflect the elastomeric layer 204. It may also be desirable to design the fluid path 206 to be symmetrical around the discontinuity 208. However, when fluid pressure in fluid path 206 is negative (under vacuum), any configuration of this component will seal, inhibiting flow in either direction.

The second layer 202 contains a recess 216 that, when assembled with the first and third layers 200 and 204, locates directly above the discontinuity 208. The alignment of the patterned features of the first and second layers allows for the displacement of the third layer 204 into the second layer 202 when pressure is applied to the fluid in the first layer 200. The geometry of the layers and patterned features (including but not limited to thickness, pattern depth and width, and feature spacing) govern the function of the component.

In one embodiment, the fluid path has the same geometry on either side of the discontinuous region (FIG. 3B). When the pressure on one side of the discontinuity in the first layer generates enough force to displace the overlapping area of the third layer into the second layer, the fluid in the first layer passes over the discontinuity into the fluid path on the other side. When the pressure drops to the level at which it can not sustain the displacement of the third layer, the third layer returns to its resting position against the first layer, rendering the fluid path discontinuous. This passive behavior works in either direction provided the pressure is enough to displace the third layer and the fluid on the other side of the fluid path. While the behavior is similar to that of a burst valve, building pressure until the resistance to flow is overcome, the fluidic diode is reversible and can return to its resting state. When fluid pressure is negative, this component will seal, inhibiting flow in either direction.

In another embodiment, the fluid path has a different geometry on either side of the discontinuous region (FIG. 3C). When the pressure on one side of the discontinuity in the first layer generates enough force to displace the overlapping area of the third layer into the second layer, the fluid in the first layer passes over the discontinuity into the fluid path on the other side. When the pressure drops to the level at which it can not sustain the displacement of the third layer, the third layer returns to its resting position against the first layer, rendering the fluid path discontinuous. This passive behavior works in one direction better than another due to the different geometries on either side of the discontinuity, and therefore the component exhibits a biased behavior to flow similar to that of a diode bias to current in an electronic circuit. More specifically, a pressure could be applied from one side and allow flow in that direction, while the same pressure would not cause flow from the other direction.

Fluidic Capacitor

Figure 4:
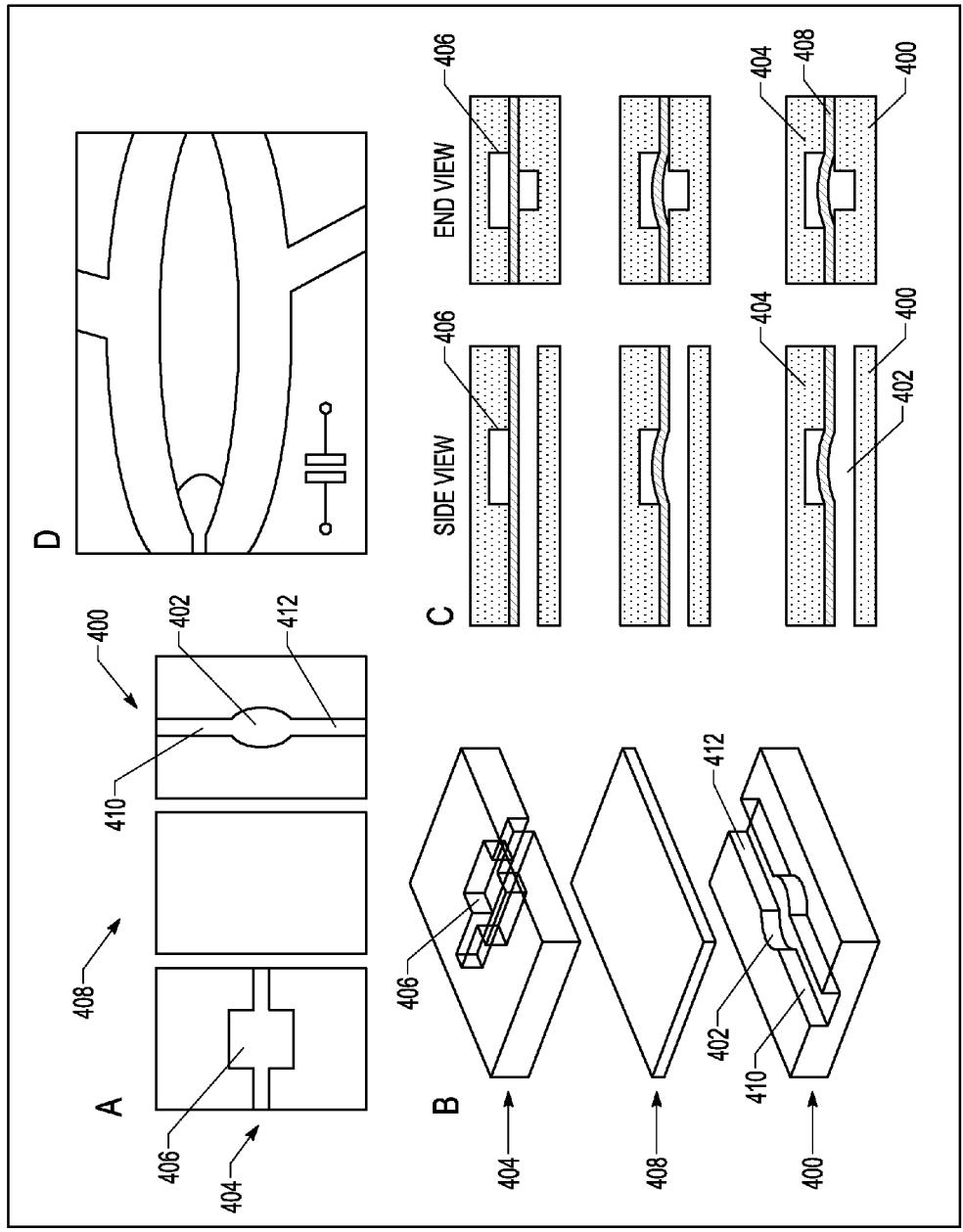
FIG. 4 is a drawing showing various views of the fluidic capacitor component. Although these embodiments present a three-layer device, it may be desirable to use multiple layer patterning in the third, elastomeric layer. (A) Overhead 2-D view of each layer. (B) 3-D view of the stacked device, showing the alignment of an enlarged fluidic chamber in layer 400 with the recess in layer 404, separated by the elastomeric layer 408. (C) Side-on and end-on views of the assembled device. In the top figure, the device is unaffected and the capacitor membrane 408 is in its resting state because the pressure difference between the fluidic path 402 and the recess 406 is equal to zero. In the middle figure, flow is directed from one-end of the device, creating a pressure difference between the fluid path 402 and the recess 406, resulting in a finite amount of stored volume under the deflected region of the elastomeric layer 408. Although the pressure difference is positive in this embodiment, the elastomeric layer 408 maintains functionality under negative pressure differences. In the bottom figure, flow is directed in the opposite direction and the behavior is the same. (D) A microscope image of the capacitor as solution is pumped into the enlarged fluidic chamber. The circuit analog is provided in the inset.
Figure 5:
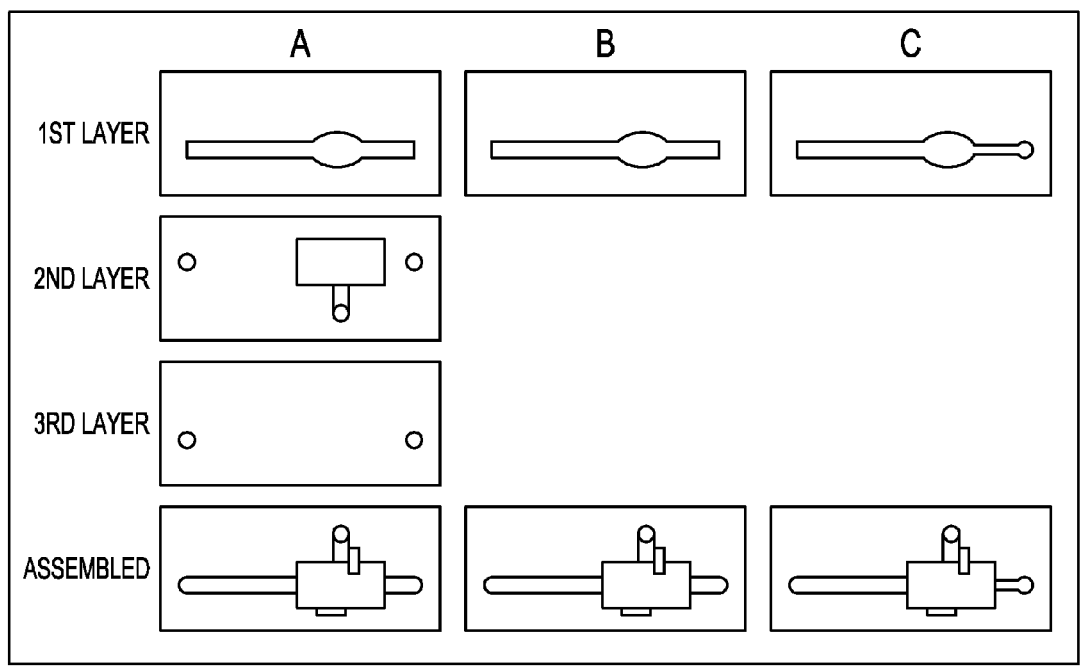
FIG. 5 is a drawing showing the top view of each of the layer of a fluidic capacitor in the three-layer embodiment. (A) Two-dimensional layout of each layer in the fluidic capacitor, along with the assembled (stacked) device. Note that the $2^{nd}$ layer is a mirror image of that in the assembled device, owing to the manner in which the surfaces are aligned and bonded. Access holes for fluid reservoirs are included in the $2^{nd}$ and $3^{rd}$ layers to bring solution to the fluid channels in the $1^{st}$ layer. An access hole that acts as a pressure ground for the capacitor component is included in the $2^{nd}$ layer. (B) An example of a fluidic capacitor where the patterned $1^{st}$ layer consists of the same geometry on either side of the enlarged fluid chamber. (C) An example of a fluidic capacitor where the patterned $1^{st}$ layer consists of a different geometry on either side of the enlarged fluid chamber. Note that the geometry is arbitrary and chosen merely for demonstration.

In one embodiment, the fluidic capacitor also contains a three layer structure as shown in FIGS. 4 and 5. Although this embodiment presents a three-layer device, it may be desirable to use multiple sublayer patterning in the third, elastomeric layer. The first layer 400 contains a continuous fluid path 402. The second layer 404 contains a patterned recess 406 that is aligned above a continuous fluid path 402 in the first layer 400, with a third layer 408 in between the first and second layers 400 and 404. Sealing the third layer against the patterned sides of the first and second layers 400 and 494 forms a three-layer device in a simplest embodiment, as shown in FIG. 4. The alignment of the patterned features of the first 400 and second 404 layers allows for the displacement of the third layer 408 into the recess 406 of the second layer 404 when pressure is applied to the fluid in the first layer. Fluid in the first layer can deflect the third layer into the recess in the second layer orthogonal to the flow and still flow across the continuous path. The geometry of the layers and patterned features (including but not limited to thickness, pattern depth and width, and feature spacing) govern the function of the component. When the pressure of the fluid in the first layer 400 generates enough force to displace the overlapping area of the third layer 408 into the recess 406 in the second layer 404, the fluid in the first layer is stored in the void created by the deflection of the elastomer (third) layer 408. When the pressure drops to the level at which it can no longer store the volume in the void created by the displacement of the third layer, the third layer 408 returns to its resting position; and all of the flow passes through the first fluid path 402. This passive behavior works in either direction provided the pressure is enough to displace the third layer and maintain the fluid flow in the first layer. Similarly, when a negative pressure (vacuum) is applied to the fluid path 402 from either direction, the third layer 408 is displaced into the fluid path 402, thereby storing a negative volume in the void created by the deflection of the elastomer (third) layer 408. In this manner, the fluidic capacitor possesses equal functionality under pressure or vacuum.

In a preferred embodiment, the cross-sectional area of the fluid path 402 is larger than that of its upstream or downstream channels 410 and 412, as shown in FIG. 4. In another embodiment, the fluid path in the first layer has the same geometry on either side of the recessed region in the second layer (FIG. 5B). In yet another embodiment, the fluid path in the first layer has a different geometry on either side of the recessed region in the second layer (FIG. 5C).

The fluidic capacitor is analogous to a capacitor in the electronic arts. With the present invention, the analogy is proposed for fluidic capacitance, C, where the elasticity of the third layer serves to store a specific volume of fluid per applied pressure. The flow rate, Q, through a fluidic capacitor is therefore defined by the following equation:

$$Q = C\frac{dP}{dt} \qquad (1)$$

Equation (1) indicates that a fluid will only flow through a capacitor when a change in pressure, P, over time, t, is observed, just as a charge only flows through an electrical capacitor when there is a change in voltage. The value of C (in units of $m^3 \, Pa^{-1}$), therefore, gives the amount of volume stored in the fluidic capacitor per applied pressure, and is dependent upon the fabrication materials, the device geometry, and the fluids used.

The capacitance (C) of the fluid capacitor may be tuned by controlling the thickness of the elastomer material and the type of elastomer. Elastomers appropriate for the present invention include, but are not limited to, polydimethylsiloxane (PDMS), polymethylmethacrylate (PMMA) polyisoprene, polybutadiene, polychloroprene, polyisobutylene, poly(styrene-butadiene-styrene), polyurethanes, silicone polymers, poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly (ethyl vinyl ether), poly(vinylidene fluoride), poly(vinylidene fluoride-hexafluoropropylene)copolymer (Viton), elastomeric compositions of polyvinylchloride (PVC), polysulfone, polycarbonate, polytertrafluoroethylene (Teflon), and blends thereof. PDMS is the preferred elastomeric material for the present invention.

Figure 16:
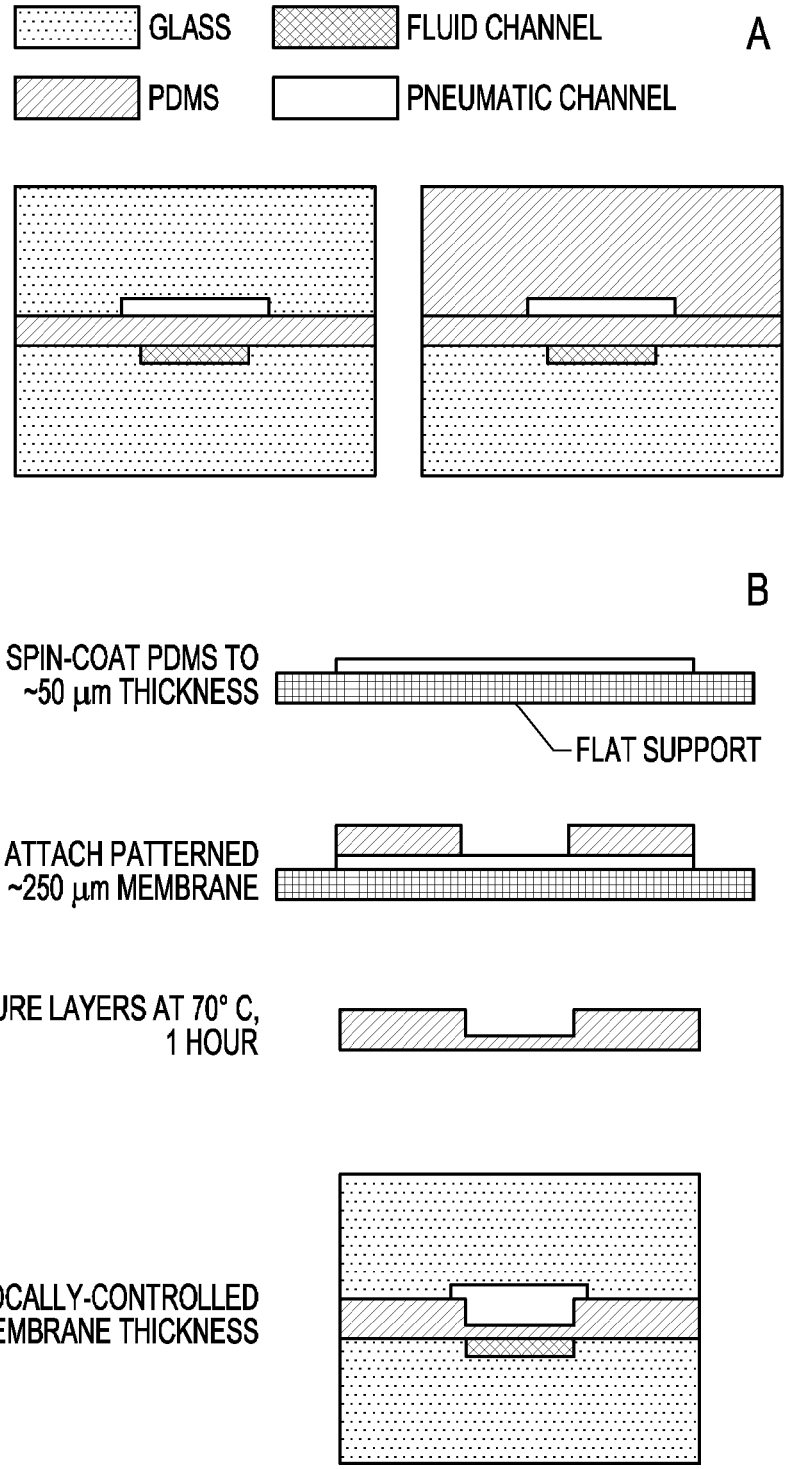
FIG. 16 is a drawing showing one method to locally control the thickness of the elastomeric layer. (A) Two possible embodiments of the typical three-layer device. (B) One fabrication method to locally control the thickness of the middle elastomeric layer. In this embodiment, precisely-localized thinned regions of elastomeric membrane are created.

In certain embodiments, the elastomeric (third) layer 408 can contain more than one sublayers. FIG. 16 is a drawing showing one method to locally control the thickness of the elastomeric layer by introducing multiple sublayers into the elastomeric layer 408. FIG. 16A shows two possible embodiments of the typical three-layer device. FIG. 16B shows one fabrication method to locally control the thickness of the middle elastomeric layer. In this embodiment, locally thinned regions are created. Fluidic capacitance in the locally thinned regions will be increased. Another embodiment of this method is to create precisely-localized thickened regions on the membrane. Fluidic capacitance in the locally-thickened regions will be decreased. Therefore, by using more than one sublayers in the elastomeric layer 408, capacitance may be controlled by thinning or thickening of the layer above the fluid path 402.

Fluidic Inductor

Figure 6:
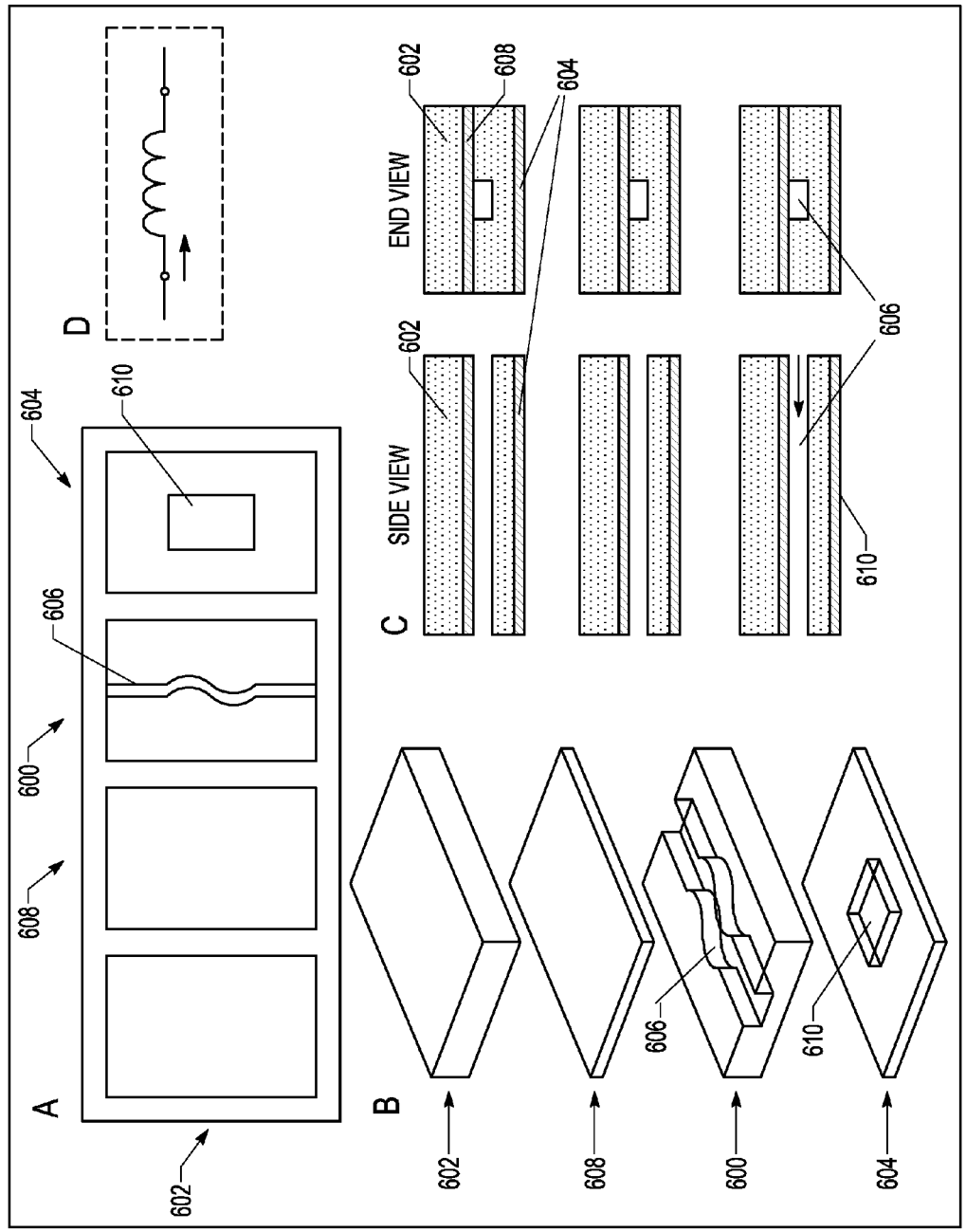
FIG. 6 is a drawing showing various views of the fluidic inductor is component. (A) Overhead 2-D view of each layer. (B) 3-D view of the stacked device, showing the alignment of a fluid channel in layer 600 (shown with an arbitrary geometry) with a heated region in layer 604. (C) Side-on and end-on views of the assembled device. In the top figure, the device is unaffected and the inductor is in its resting state. In the middle figure, flow is directed from one-end of the device over the heated region and in the bottom figure, flow is directed in the opposite direction with the same behavior. (D) The inductor analog.

The fluidic inductor (FIG. 6) is a three layer structure, where the second layer 602 is aligned above a continuous fluidic path 606 in the first layer 600, with a third layer 604, sealing against the first or second layer 600 or 602. The third layer 604 comprises a temperature-controlled plate 610 mated with the first fluidic layer to provide a means of heat transfer from the third layer 604 to the fluid. The alignment of the patterned features of the first layer with those of the third layer allows for localization of heated regions on the device. Fluid in the fluid path 606 that is heated by the third layer 604 possesses a lower density at equilibrium than the remainder of the solution in the first layer. Any changes in flow will be influenced by the changing density at the heated regions. The geometry of the first layer is such that the entering fluid will be heated more slowly than the exiting solution will be cooled. The geometry of the layers and patterned features (including but not limited to thickness, pattern depth and width, and feature spacing) govern the function of the component. As illustrated in FIG. 6, an optional fourth layer 608 of elastomeric material may be present. This optional layer simplifies construction of the µ-TAS that also contains other passive structures, such as the fluidic diode and the fluidic capacitor discussed above. When the pressure of the fluid in the first layer induces flow in the heated is regions, the heat energy is transferred from the fourth layer into the entering fluid, and the heat energy is transferred from the departing heated fluid into the substrate of the first layer. Because of the specific geometry of the inductor, the heat is transferred more rapidly from the departing heated fluid into the substrate of the first layer than is transferred from the fourth layer into the entering fluid. This difference in heat transfer properties gives a phase shift between input and output pressures and defines the behavior of the component.

Figure 7:
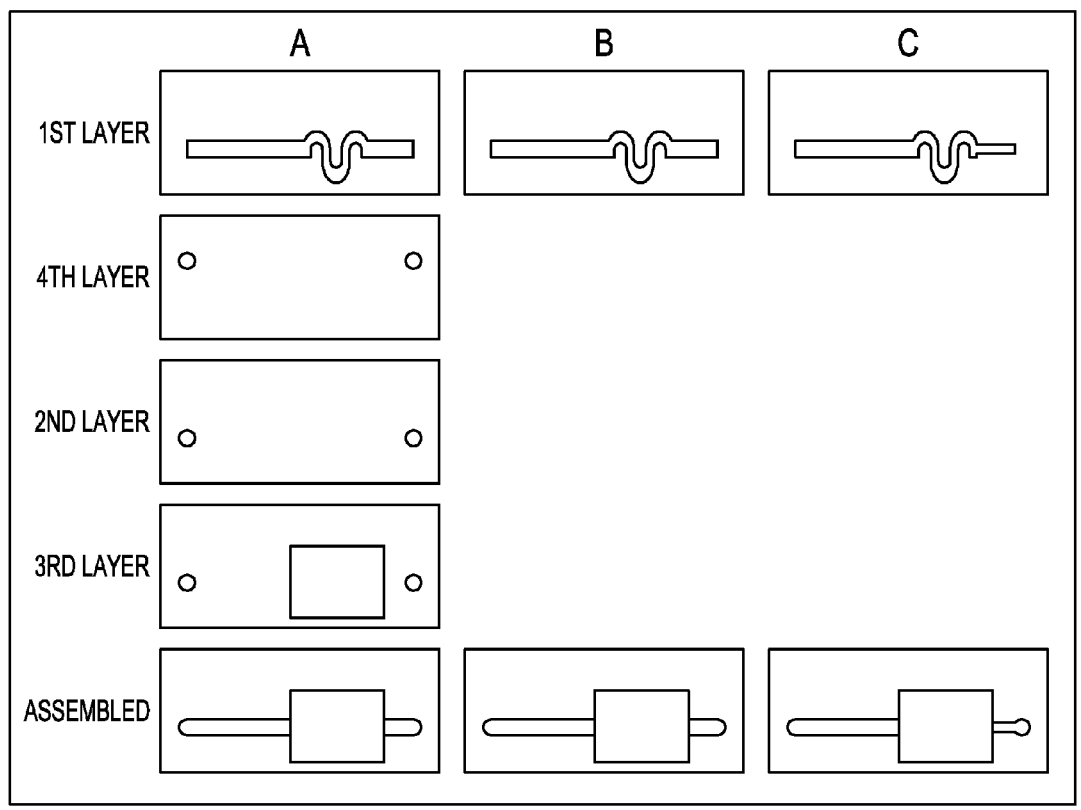
FIG. 7 is a drawing showing the top view of each of the layer of a fluidic inductor. (A) Two-dimensional layout of each layer in the fluidic inductor, along with the assembled (stacked) device. Note that the $2^{nd}$ layer is a mirror image of that in the assembled device, owing to the manner in which the surfaces are aligned and bonded. Access holes for fluid reservoirs are included in the $2^{nd}$ and $3^{rd}$ layers to bring solution to the fluid channels in the $1^{st}$ layer. (B) An example of a fluidic inductor where the patterned $1^{st}$ layer consists of the same geometry on either side of the thermal region. (C) An example of a fluidic inductor where the patterned $1^{st}$ layer consists of a different geometry on either side of the thermal region. Note that the geometry is arbitrary and chosen merely for demonstration.

In a preferred embodiment, the heated region of the fluid path 606 preferably contains a sinuous path to increase the amount of fluid being heated. In another embodiment, the fluid path in the first layer has the same geometry on either side of the heated region in the fourth layer (FIG. 7B). In yet another embodiment, the fluid path in the first layer has a different geometry on either side of the heated region in the fourth layer (FIG. 7C).

In either aforementioned embodiment, the fluidic inductor is proposed to be analogous to an inductor in the electronic arts. With the present invention, the analogy is proposed for fluidic inductance, L, where the density of the fluid in the first layer serves to store a specific volume of fluid per applied volumetric flow rate, Q. The pressure drop, ΔP, through a fluidic inductor is therefore defined by the following equation:

$$\Delta P = L\frac{dQ}{dt} \qquad (2)$$

Equation (2) indicates that a pressure drop will only be induced through an inductor when a change in volumetric flow rate, Q, over time, t, is observed. This is similar to an electrical inductor, where a voltage drop is only induced when there is a change in current. The value of L (in units of $kg \, m^{-4}$) includes a density term (in $kg \, m^{-3}$), which highlights the temperature dependence of the fluidic inductor due to the temperature dependence of fluid density. This term is dependent upon the fabrication materials, the device geometry, the temperature of the plate, and the fluids used. Fluidic inductance can be tuned by altering the heat transfer properties of the entrance or exit channels, by altering the temperature of the plate, or by altering the type and identity of fluid used. Similarly, inductance can also be tuned by changing the geometry of the fluid path. In certain embodiments, the fluid path can be smaller or larger in cross sectional area than its upstream or downstream channels. In other embodiments, the fluid path can be lengthened by a sinuous path.

This behavior is not limited to localization of heated regions. The third layer 604 of this component could also contain localized cooled regions, in which case the heat flow characteristics of the fluidic inductor would be in the opposite direction.

Fluidic Resistor

Resistance to fluid flow in a microchannel is analogous to electrical resistance and is described by the following equation (S. Attiya et al., 2001, *Electrophoresis* 22:318)

$$\Delta P = \frac{Q}{A}\left(\frac{\eta L}{wdf}\right) = Q\left(\frac{4\eta L}{(wd)^2 F}\right) \quad (3)$$

where $\Delta P$ is the pressure drop along the microchannel; Q is the flow rate; and $(4\eta L)/[(wd)^2 F]$ is the resistance (R) (w, d, and L are the half-width, half-depth, and length of the microchannel; $\eta$ is the viscosity of the fluid; and F is a geometric form factor, in the case of microchannels, F 0.0566 dwr$^3$ − 0.262 dwr$^2$+0.347 dwr−0.000699, where dwr is the depth to width ratio). Equation 3 is analogous to the electrical resistor where V=IR. Further, according to equation 3, the fluidic resistor can be tuned by varying the length, width, depth, or form factor of the microchannel.

Microfluidic Circuits

The passive components described above can be used in combination in a microfluidic circuits to achieve results similar to an electrical circuit. These microfluidic circuits can be used to rectify fluid flow, eliminating negative flow typically associated with valve-based micropumps; and to control directions and flow rates in a µ-TAS without requiring externally controlled instrumentations. Importantly, a properly designed microfluidic circuit facilitates control of flow rates and directions only by varying the input frequency, usually that of the pump.

Fluidic Rectifier

Figure 8:
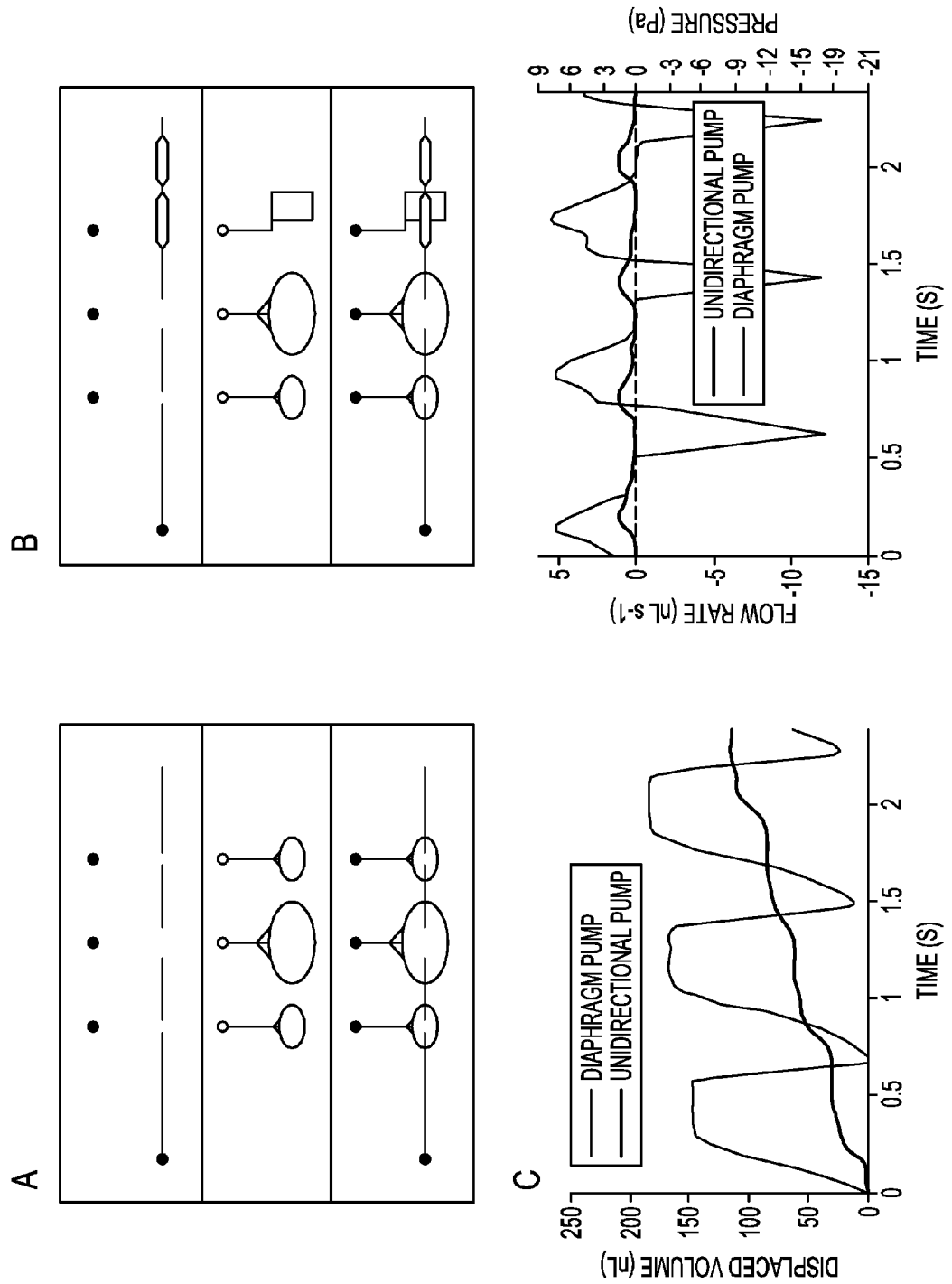
FIG. 8 are drawings and graphs showing the result and design of a fluidic rectifier. (A) Prior art design for a diaphragm pump consisting of three active valves. The top image represents the fluid layer, the middle the valve layer, and the bottom an overlay of the two. (B) Proposed design for a half-wave rectifier using based on a similar pump design consisting of two active valves and a passive diode component that imparts directionality. (C) Volumetric displacement and flow/pressure profiles in time comparing the prior art 3-valve diaphragm pump to the proposed 2-valve pump with fluidic diode (half-wave rectifier).

In one embodiment, an input pressure source (micro-fluidic diaphragm pump, syringe pump, etc.) could be combined with the passive diode to eliminate negative flow (or 'pullback'). For example, diaphragm or peristaltic pumps made from three or more micro-fluidic valves possess an inherent flow reversal due to the cyclic nature of the pumping. Though the overall volumetric flow is positive, there exist negative flow regions in each pumping cycle which could be detrimental to many applications requiring smooth delivery of fluid. It would be desirable to place a passive micro-fluidic diode in series with this type of pump to eliminate the flow reversal problem—allowing flow in the positive direction only—while simultaneously reducing the number of valves necessary for a diaphragm pump. This action would be similar to a half-wave flow rectifier in electrical circuitry. FIG. 5A shows the design described by prior art of a three-valve micro-fluidic diaphragm pump. FIG. 8B shows the fluidic diode, described in the present invention, where a fluidic diode is placed in series with the diaphragm pump. FIG. 5C shows the measured volumetric displacements and flow rates for each configuration. These measurements clearly show that the fluidic diode behaves as predicted, acting here as a half-wave flow rectifier. The fluidic circuit is therefore referred to as a unidirectional micro-fluidic pump. Note also that the inclusion of the fluidic diode eliminates the need for the exiting gate valve in the micro-fluidic diaphragm pump, thereby reducing the number of control lines needed. In certain embodiments, the fluidic diode can eliminate the need for both the entry and exit gate valves, producing a unidirectional pump using only one active valve.

In yet another embodiment, an input pressure source could be combined with several passive diodes to function as a full-wave flow rectifier.

In another embodiment, an input pressure source could be combined with several passive diodes to function as a bridge rectifier.

Fluidic Frequency Filter

Figure 9:
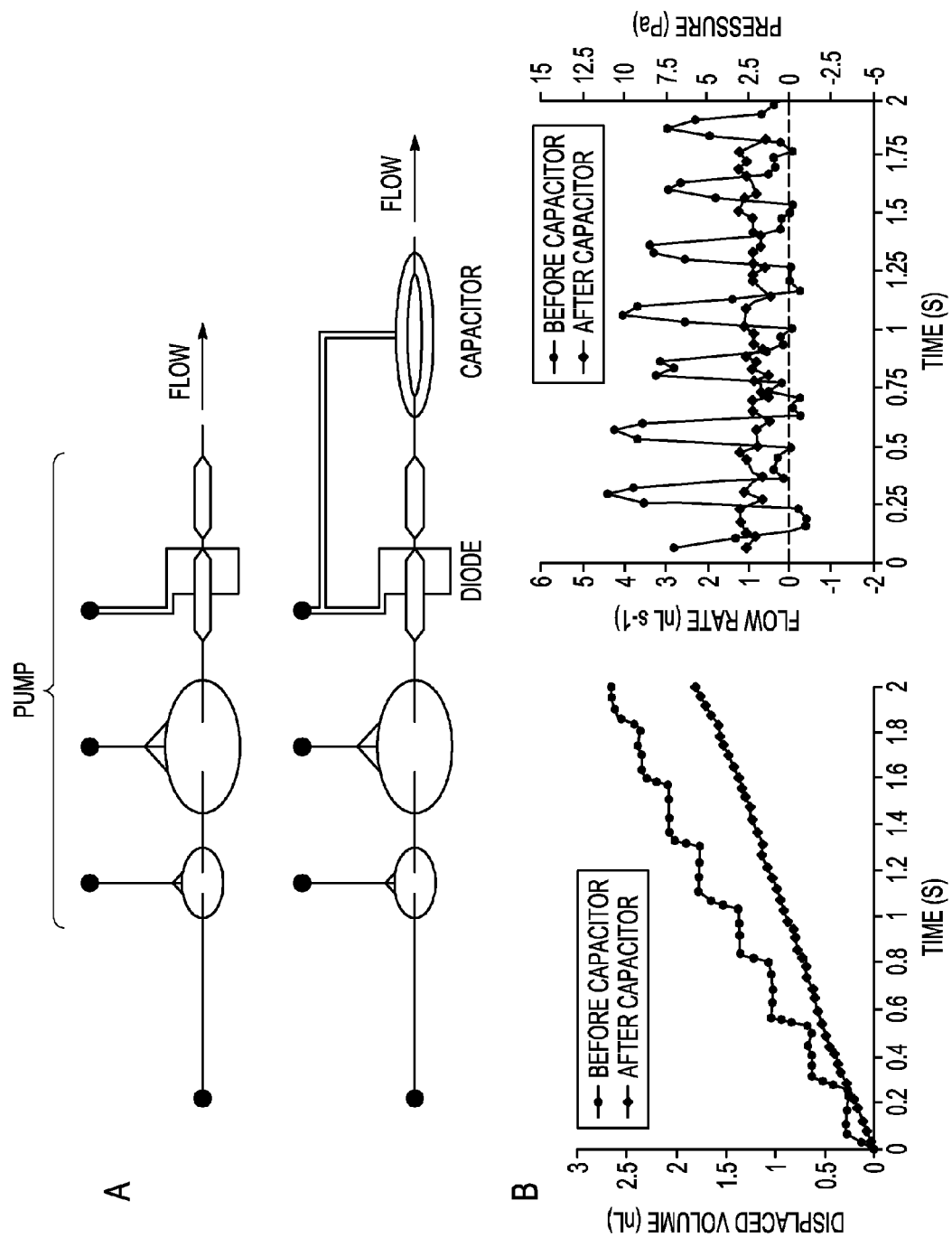
FIG. 9 are drawings and graphs showing the result and design of a flow profile converter. (A) Unidirectional pump using a fluidic diode (top) and the same pump combined with a fluidic capacitor that acts as a low-pass filter. Note the shared connection of the diode and capacitor (gray) to a single ground line. (B) Volumetric displacement and flow/pressure profiles vs. time of the pump alone and the low-pass filter design (~0.2 Hz cutoff) using a fluidic capacitor to dampen the square wave oscillations (4.0 Hz).

In another embodiment, an input pressure source could be combined with the passive diode and inductor or capacitor to function as a flow profile converter. Essentially, a microfluidic capacitor (or inductor) could be placed in parallel (or in series) with the unidirectional micro-fluidic pump above to dampen the flow, providing means for energy storage in the form of fluid volume. With these types of components, the pulsating, multidirectional flow profile from a typical diaphragm pump could be converted or shaped into a smooth, unidirectional flow profile in a manner analogous to AC-to-DC transformers in the electronic arts. Thus, the flow control of small volumes (microliter, nanoliter, picoliter, etc.) could be greatly enhanced while significantly reducing the complexity of the control instrumentation. For example, FIG. 9 shows a fluidic capacitor arranged in parallel with the unidirectional micro-fluidic pump from above to give a microfluidic low-pass filter configuration. FIG. 9A shows the patterned channel structures of this embodiment. FIG. 9B shows the measured volumetric displacements and flow rates from both the unidirectional pump (before capacitor) and the dampened flow (after capacitor). The input flow was pulsed at 4.0 Hz, which was clearly filtered out of the output from the capacitor. The micro-fluidic low-pass filter shown here was measured to have a frequency cutoff, $f_0$, of approximately ~0.2 Hz. This embodiment could also function as an integrator of the input pressure profile. Furthermore, the frequency response of this embodiment could allow preferential flow in specific directions based on the input frequency.

Figure 10:
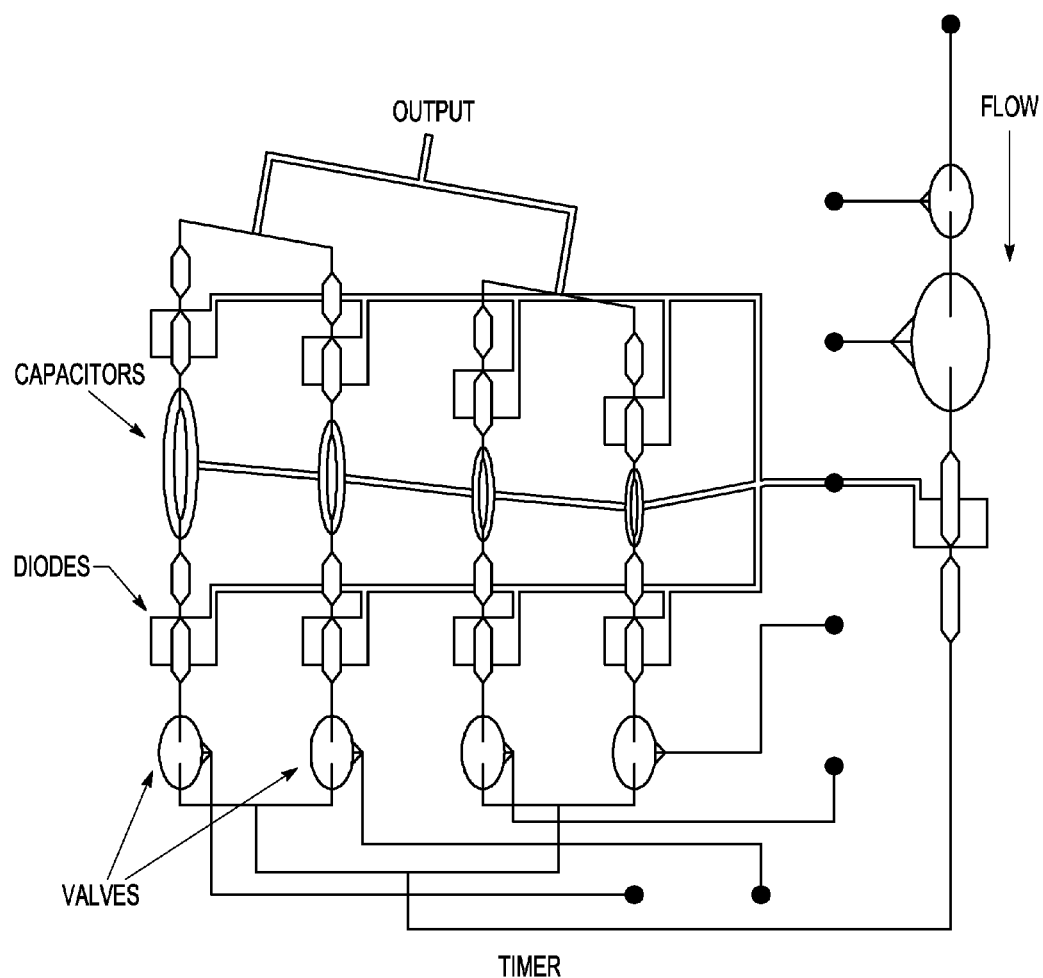
FIG. 10 is a drawing showing an embodiment of a combined device consisting of a half-wave rectifier, diodes, and various capacitors to create a timing circuit based upon four low-pass filters arranged in parallel with a shared output.

In another embodiment, a combined device consisting of a half-wave rectifier, diodes, and various capacitors is arranged to create a timing circuit (FIG. 10) based upon four low-pass filters arranged in parallel with a shared output.

In another embodiment, an input pressure source could be combined a fluidic capacitor in series or a fluidic inductor in parallel to provide a micro-fluidic high-pass filter configuration. This embodiment could also function as a differentiator of the input pressure profile. Furthermore, the frequency response of this embodiment could allow preferential flow in specific directions based on the input frequency. This embodiment could also be combined with the fluidic diode to impart directional nature to the flow.

In another embodiment, an input pressure source could be combined with a fluidic capacitor in parallel or a fluidic inductor in series to provide a micro-fluidic high-pass filter configuration. This embodiment can also function as an integrator of the input pressure profile. Furthermore, the frequency response of this embodiment could allow preferential flow in specific directions based on the input frequency. This embodiment could also be combined with the fluidic diode to impart directional nature to the flow.

Figure 11:
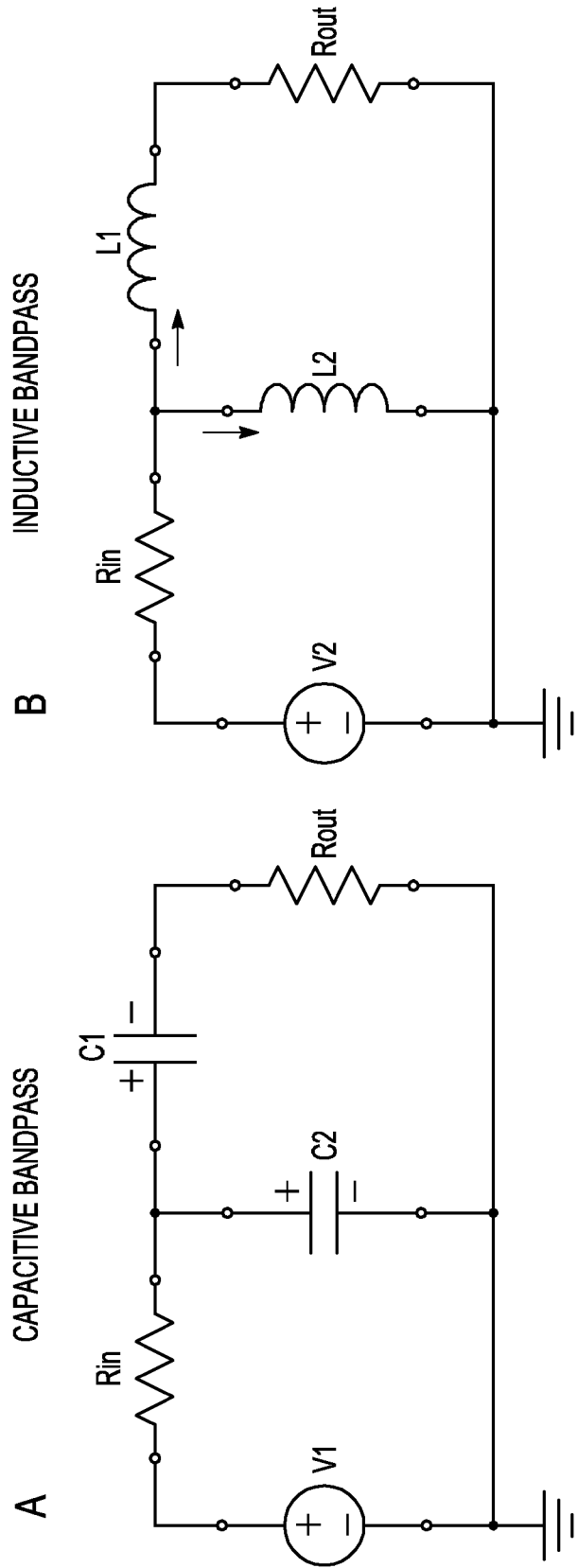
FIG. 11 are drawings showing two embodiments of a band-pass filter created from passive fluidic components are presented, using a combination of fluidic resistors (channels) coupled with either (A) capacitors or (B) inductors.

In another embodiment a bandpass filter can be created from passive fluidic components using a combination of an input pressure source with fluidic resistors (channels)

coupled with either capacitors (FIG. 11A) or inductors (FIG. 11B). This embodiment could also be combined with the fluidic diode to impart directional nature to the flow.

Passive Fluidic Timer

Figure 12:
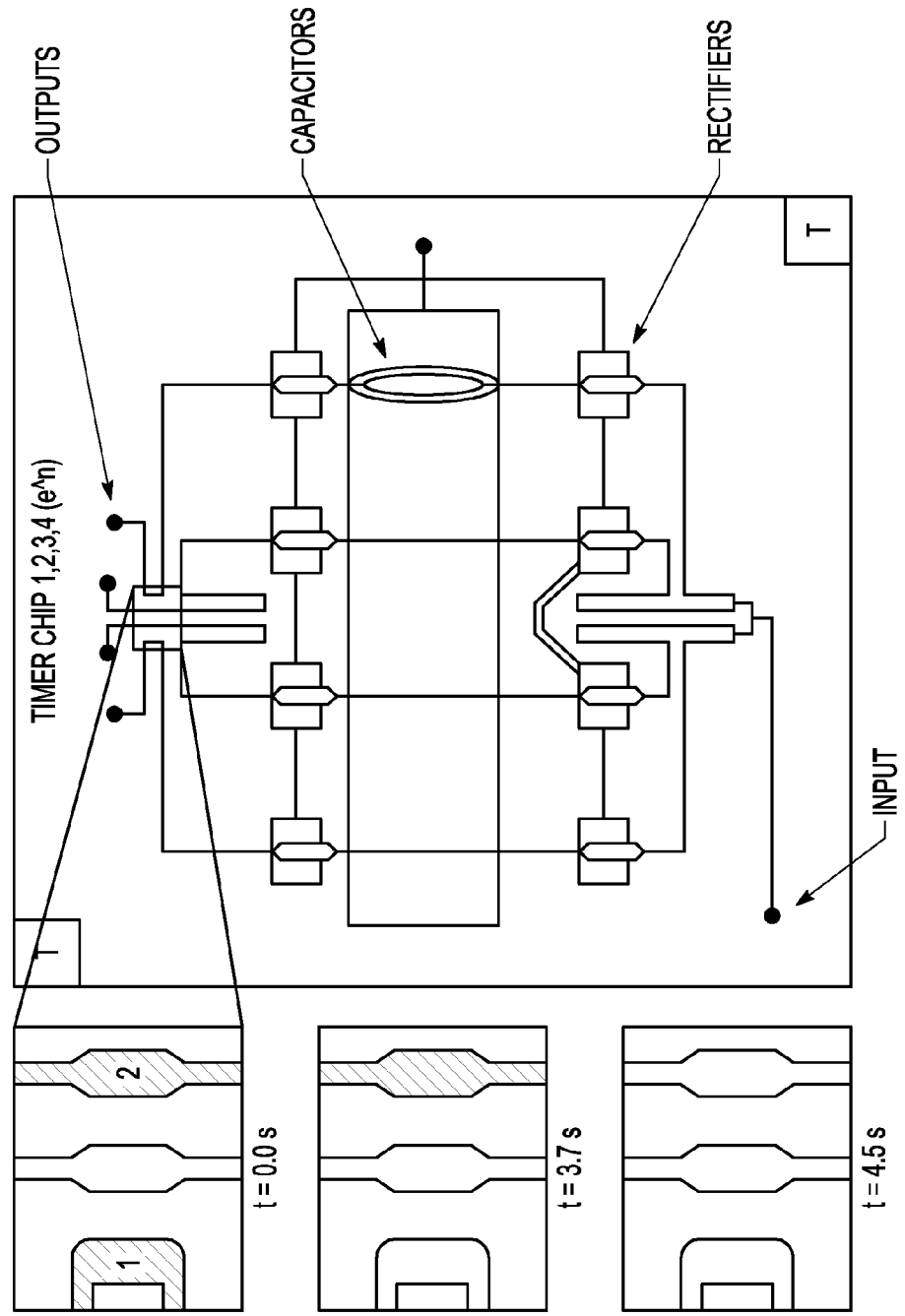
FIG. 12 are a drawing and pictures showing an entirely passive, pre-programmed fluidic timing device. The device design is shown along with CCD images of the timed breakthrough of flows in two different paths from the same input source.

In one embodiment, a fluidic timer can be developed using combinatorial fluidic circuits, which enables passive timing on a microfluidic device, where the flow behavior is pre-programmed into the device architecture, without requiring external controls. A sample mask design for this device is given in FIG. 12. The device contains of a single syringe pump input that was split into four fluidic paths, each consisting of a capacitor flanked by two rectifiers. The concept of the timing circuit is that the different charging times of the capacitors (different fluidic capacitance) result in different breakthrough times through the output rectifier. In the absence of such passive components in the circuit, flow through all of the output fluidic channels (resistors) would initiate at the onset of syringe pump flow. However, because the to capacitors function as designed, the output flows are selectively delayed with a single constant input flow. As shown in FIG. 12, two of the flow paths are shown, With syringe pump flow initiated at t=0.0, solution in path 1 began flowing at $t_1$, (for example, t=3.7 s), and solution in path 2 began flowing at $t_2$ (for example, t=4.5 s).

Passive Pressure Meter

Figure 13:
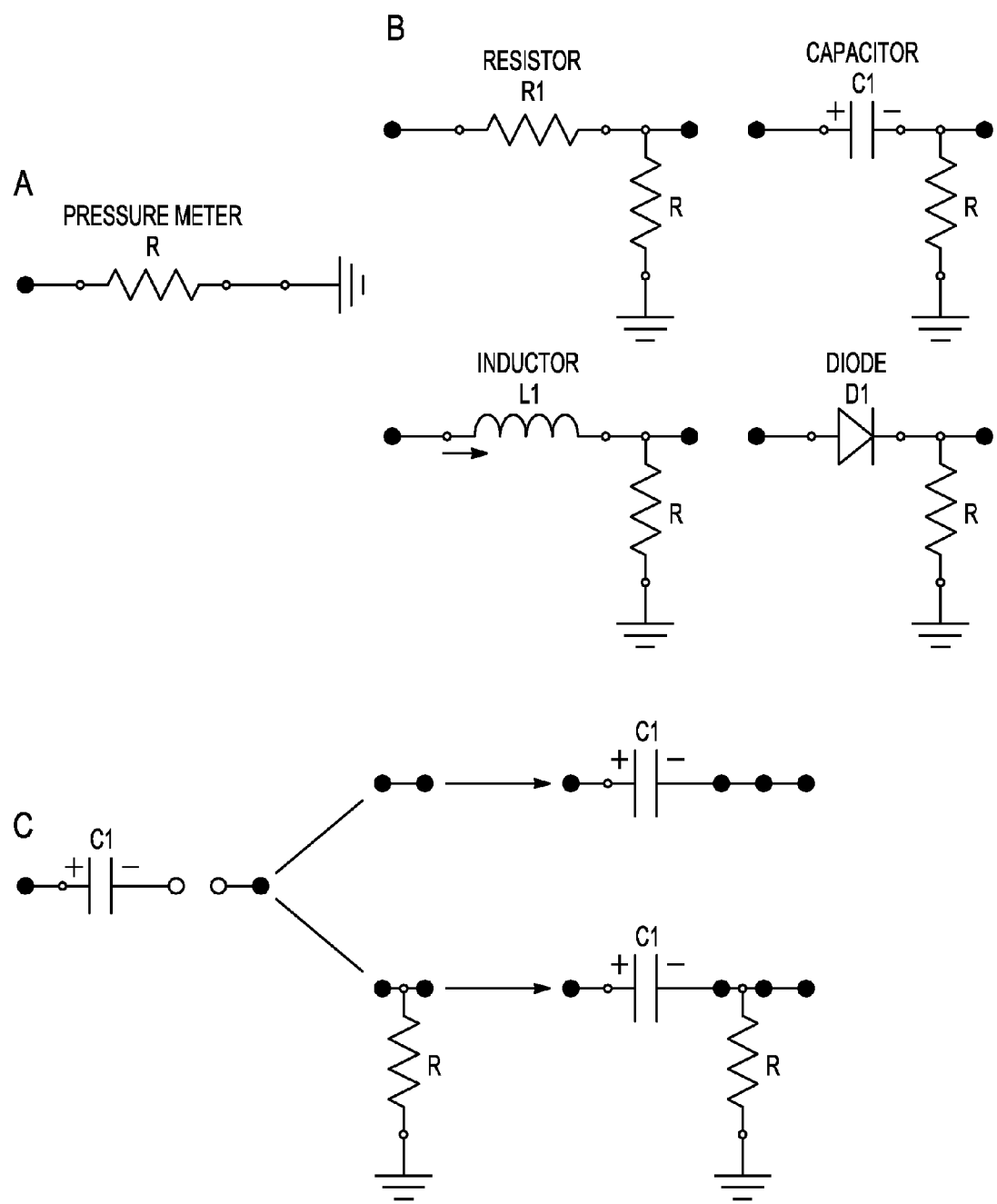
FIG. 13 are drawings showing various embodiments of the resistance pressure meter. (A) A representation for the fluidic pressure meter, where a large resistance is fabricated through channel dimension and geometry and connected to ground, where flow can be interrogated to provide pressure information. (B) The pressure meter connected to various fluidic components to demonstrate its utility in analyzing and characterizing a microfluidic circuit. (C) A sample component with built-in discontinuity for flexible testing. Under normal operation (top) the fluidic channel is bridged by a short channel. For testing or troubleshooting, the fluidic channel is bridged by a short channel connected to a pressure meter (bottom). Note that the pressure meter is modular and can be used on any component in any circuit provided the discontinuity is patterned into the fluid layer.

In order to measure and characterize the various devices presented and alluded to here, a fluidic pressure meter is presented (FIG. 13), where a large resistance (relative to the channel being measured, at least 10 times larger, preferably 100-1000 times larger) is fabricated through channel dimension and geometry and connected to ground (atmospheric pressure), where flow can be interrogated to provide pressure information. The pressure meter is constructed of three layers, similar to the fluidic capacitor described above. The fluid path of the pressure meter, however, is designed to be high resistance. This usually means that the depth and/or width of the fluid path is much smaller and that of the main channel where the pressure is to be interrogated, The deflection of the elastomeric layer into the recess of the top (second) layer (which is connected to atmospheric pressure) is proportional to the pressure in the fluid path and can be measured using a distance measurement technique, for example, an extrinsic Fabry-Perot interferometer (EFPI).

The pressure meter can be connected to various fluidic components for analyzing and characterizing a micro-fluidic circuit (FIG. 13B). An embodiment of a sample component with built-in discontinuity for flexible testing is presented in FIG. 13C. Under normal operation (top) the fluidic channel is bridged by a short channel. For testing or troubleshooting, the fluidic channel is bridged by a short channel connected to a pressure meter (bottom). Note that the pressure meter is modular and can be used on any component in any circuit provided the discontinuity is patterned into the fluid layer.

Without further description, it is believed that one of ordinary skill in the art can, using the preceding description and the following illustrative example, make and utilize the compounds of the present invention and practice the methods. The following example is given to illustrate the present invention. It should be understood that the invention is not to be limited to the specific conditions or details described in the example.

Example

Because frequency dependence could be designed into the microfluidic architecture using passive components, it became clear that the characteristic frequency of these networks is controllable. If so, it was hypothesized that relative flow rates of individual flow paths within the same networks could be metered in a valveless, unhindered flow network. It was postulated that the characteristic frequency of the fluidic networks could be shifted by simply altering the capacitance in the fluidic circuit.

Figure 14:
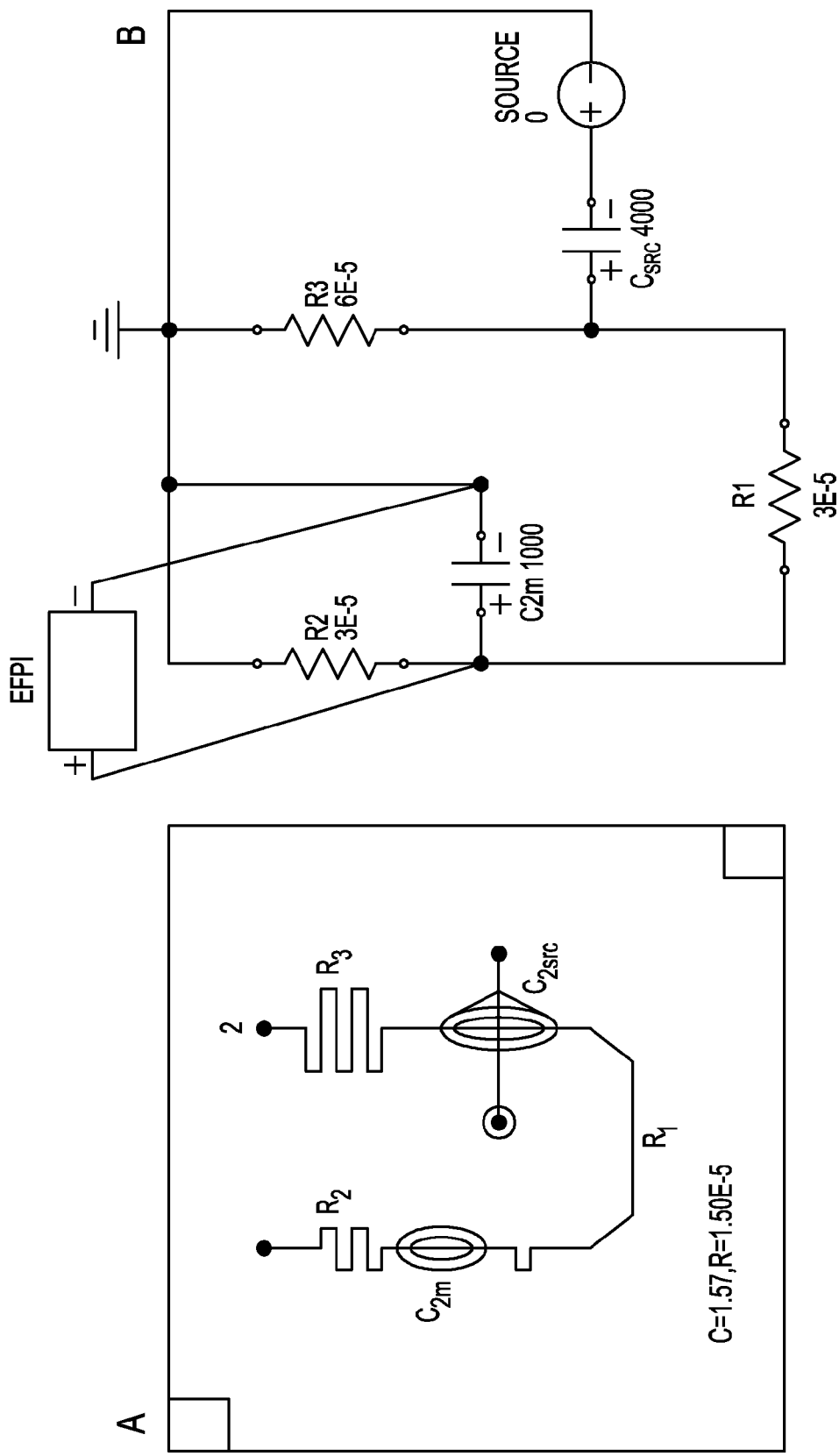
FIG. 14 are (A) a drawing showing a microdevice design arranged into a band-pass configuration with resistors (labeled as R) and capacitors (labeled as C); and (B) its electrical circuit equivalent.

A new microdevice with unbroken fluidic networks (no valved flow paths) was designed. As shown by the mask designs in FIG. 14A, in lieu of a valve-based pump, the device included a single actuation chamber above a capacitor (the 'source capacitor'), several fluidic resistors, as well as an additional capacitor (the 'measurement capacitor') isolated from the source by a resistor. The electrical circuit equivalent to the new design is shown in FIG. 14B (where the resistances are reported in Pa s $\mu m^{-3}$, capacitances in $\mu m^3$ $Pa^{-1}$), with the EFPI measurement illustrated by a multi-meter device over the measurement capacitor. Note that in the fluidic circuit (FIG. 14A) the capacitors appear to be arranged in series with the resistors (R2 and R3); however, in the electrical circuit equivalent (FIG. 14B), the capacitors are in parallel with these resistors. This is because in the fluidic capacitor stores fluid in a direction perpendicular to the direction of fluid flow. As such, although it is fluidly in series with the resistor, the electrical analog is in parallel. In this application, where "series" and "parallel" are mentioned, it is in the fluidic sense rather than its electrical equivalent. The layout of this fluidic circuit places the input waveform from the vacuum or pressure source in series with capacitor $C_{2src}$ and in parallel with capacitor $C_{2m}$, resulting in a band-pass filter configuration.

The frequency response of this device was measured using EFPI to visualize the deflection of the measurement capacitors. Vacuum pulses at various frequencies were applied to the source capacitor ($C_{2src}$), while the EFPI sensor was used to measure the deflection of the membrane of capacitor $C_{2m}$ in a non-contact manner.

Figure 15:
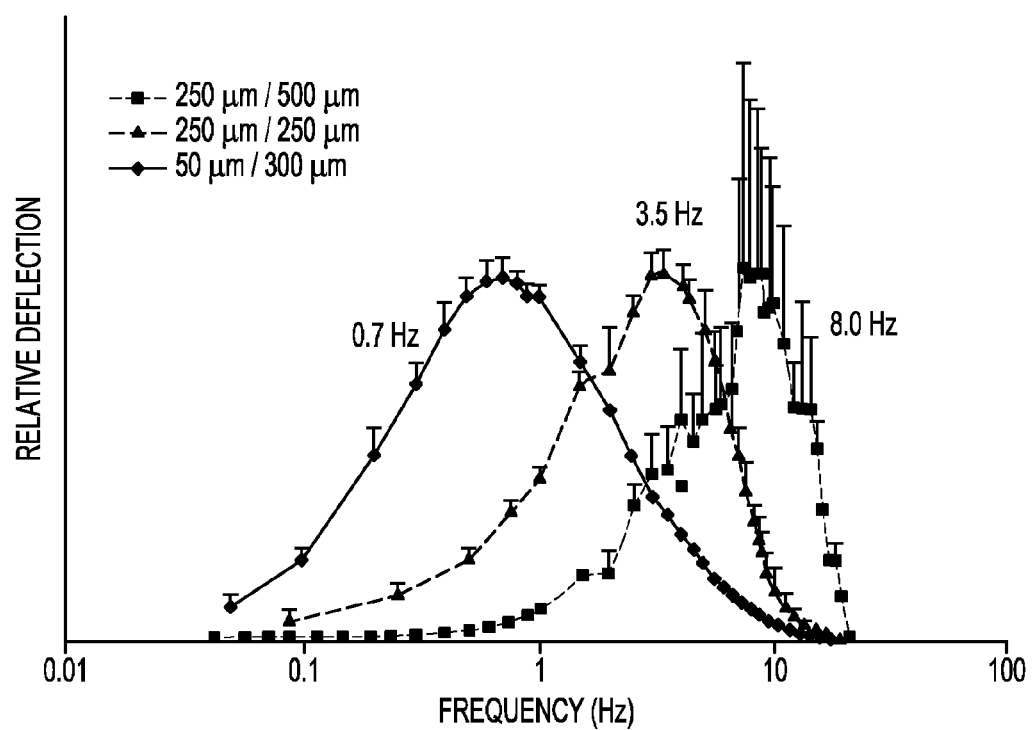
FIG. 15 is a graph showing that characteristic frequencies of the band-pass fluidic circuit (such as that of FIG. 15) could be shifted by over an order of magnitude by locally altering the PDMS membrane thicknesses at the capacitor region. Different curves represent different combinations of the thicknesses.

By varying the thickness of the elastomeric layer of the capacitor (using the method outlined in FIG. 16), the characteristic frequency can be shifted significantly. FIG. 15 shows the results of three combinations of capacitor membrane thicknesses using the same device design of FIG. 14: 1) ~50 μm membrane at $C_{2m}$ and ~300 μm at $C_{2src}$; 2) ~250 μm membrane at both $C_{2m}$ and $C_{2src}$; and 3) ~250 μm membrane at $C_{2m}$ and ~500 μm at $C_{2src}$; whose frequency responses were evaluated using EFPI. By varying the capacitance and resistance using the passive components, the characteristic frequencies of fluidic networks can be shifted. This enables the ability to control flow rates and direction of fluids in a μ-TAS with a single input source by varying the input frequency, eliminating the need for the instrumentation that is usually necessary for microfluidic valving.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A fluidic capacitor comprising
   a first layer having a continuous fluid path thereon;
   a second layer having a recess thereon;
   a third layer of elastomeric material, wherein the third layer is sandwiched between the first layer and second layer such that the recess is in direct alignment with the fluid path, the recess fluidically isolated from the continuous fluid path by the elastomeric material;

wherein the continuous fluid path, the recess on the second layer, and the elastomeric material are configured to control a fluid flow rate through the continuous fluid path on the first layer in response to a predetermined frequency of a time-varying fluid input pressure imposed on a fluid in the continuous fluid path.

2. The fluidic capacitor of claim 1, wherein the fluid path of the capacitor is larger than that of its upstream or downstream channels.

3. The fluidic capacitor of claim 1, wherein the thickness of the elastomeric layer is about 5 μm-10 mm.

4. The fluidic capacitor of claim 1 wherein the first and second layer are made of a material selected from the group consisting of silicon, glass, ceramics, polymers, metals, and quartz.

5. The fluidic capacitor of claim 1, wherein the elastomeric material is selected from the group consisting of polydimethylsiloxane (PDMS), polymethylmethacrylate (PMMA) polyisoprene, polybutadiene, polychloroprene, polyisobutylene, poly(styrene-butadiene-styrene), polyurethanes, silicone polymers, poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly (ethyl vinyl ether), poly(vinylidene fluoride), poly (vinylidene fluoride-hexafluoropropylene)copolymer (Viton), elastomeric compositions of polyvinylchloride (PVC), polysulfone, polycarbonate, polytertrafluoroethylene (Teflon), and blends thereof.

6. The fluidic capacitor of claim 1, wherein $$Q = C\frac{dP}{dt}$$

where Q is the fluid flow rate, C is the capacitance of the capacitor, and dP/dt is the change in fluid pressure over time.

7. The fluidic capacitor of claim 1, wherein the third layer comprises at least two sublayers.

8. A microfluidic circuit comprising a fluidic capacitor, wherein the fluidic capacitor comprises
   (i) a first layer having a continuous fluid path thereon;
   (ii) a second layer having a recess thereon;
   (iii) a third layer of elastomeric material, wherein the third layer is sandwiched between the first layer and second layer such that the recess is in direct alignment with the fluid path, the recess fluidically isolated from the continuous fluid path by the elastomeric material; and
   wherein the continuous fluid path, the recess on the second layer, and the elastomeric material are configured to modulate a fluid flow rate through the continuous fluid path on the first layer in response to a predetermined frequency of a time-varying fluid input pressure imposed on a fluid in the continuous fluid path.

9. The microfluidic circuit of claim 8, further comprising a fluidic inductor, wherein the fluidic inductor comprises
   (i) a first layer having a continuous fluid path thereon;
   (ii) a second layer adjacent to the first layer and enclosing the fluid path; and
   (iii) a third layer sealing against the first or second layer and having a heating or cooling element thereon, wherein the heating or cooling element is in direct alignment with the fluid path.

10. The microfluidic circuit of claim 9, wherein the fluidic capacitor and fluidic inductor are in series or parallel.

11. A method for controlling flow rate and direction of fluid in a micro-total analysis system (μ-TAS) comprising the steps of
   providing the microfluidic circuit of claim 8; and
   pumping fluid through the microfluidic circuit at varying flow rates.

12. The method of claim 11, wherein the microfluidic circuit further comprising a fluidic inductor, wherein the fluidic inductor comprises
   (i) a first layer having a continuous fluid path thereon;
   (ii) a second layer adjacent to the first layer and enclosing the fluid path; and
   (iii) a third layer sealing against the first or second layer and having a heating or cooling element~thereon, wherein the heating or cooling element is in direct alignment with the fluid path.

13. The method of claim 12, wherein the fluidic capacitor and fluidic inductor are in series or parallel.

14. The method of claim 11, wherein the pumping step takes place at a predetermined frequency.

* * * * *